(12) United States Patent
Velaparthi et al.

(10) Patent No.: US 9,145,419 B2
(45) Date of Patent: Sep. 29, 2015

(54) IMIDAZOPYRIDAZINYL COMPOUNDS

(75) Inventors: Upender Velaparthi, Cheshire, CT (US); Peiying Liu, Madison, CT (US); James Aaron Balog, Lambertville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 166 days.

(21) Appl. No.: 13/643,555

(22) PCT Filed: Apr. 27, 2011

(86) PCT No.: PCT/US2011/034076
§ 371 (c)(1),
(2), (4) Date: Oct. 26, 2012

(87) PCT Pub. No.: WO2011/137155
PCT Pub. Date: Nov. 3, 2011

(65) Prior Publication Data
US 2013/0045980 A1    Feb. 21, 2013

Related U.S. Application Data

(60) Provisional application No. 61/328,785, filed on Apr. 28, 2010.

(51) Int. Cl.
C07D 487/04 (2006.01)
A61K 31/5025 (2006.01)
C07D 487/14 (2006.01)

(52) U.S. Cl.
CPC ................................. *C07D 487/14* (2013.01)

(58) Field of Classification Search
CPC . C07D 487/04; A61K 31/519; A61K 31/5025
USPC .......................................... 544/236; 514/248
See application file for complete search history.

(56) References Cited

U.S. PATENT DOCUMENTS

| | | | |
|---|---|---|---|
| 2004/0082781 A1 | 4/2004 | Hibi et al. | |
| 2005/0229333 A1 | 10/2005 | Glenn, Jr. et al. | |
| 2006/0154105 A1 | 7/2006 | Yamamoto et al. | |
| 2007/0049591 A1 | 3/2007 | Pinkerton et al. | |
| 2011/0269752 A1* | 11/2011 | Pastor-Fernandez et al. | 514/232.5 |

FOREIGN PATENT DOCUMENTS

| | | |
|---|---|---|
| EP | 1 277 754 | 1/2003 |
| WO | WO 98/08847 | 3/1998 |
| WO | WO 2005/051906 | 6/2005 |
| WO | WO 2005/080355 | 9/2005 |
| WO | WO 2007/038314 | 4/2007 |
| WO | WO 2007/095588 | 8/2007 |
| WO | WO 2008/014219 | 1/2008 |
| WO | WO 2008/016192 | 2/2008 |
| WO | WO 2008/019309 | 2/2008 |
| WO | WO 2008/030579 | 3/2008 |
| WO | WO 2008/133192 | 11/2008 |
| WO | WO 2009/017954 | 2/2009 |
| WO | WO 2009/060197 | 5/2009 |
| WO | WO 2009/100375 | 8/2009 |
| WO | WO 2009/115321 | 9/2009 |

OTHER PUBLICATIONS

Chinese Office Action and Search Report issued Apr. 1, 2014 (w/ English translation).
International Preliminary Report on Patentability for PCT/US2011/034076 issued Oct. 30, 2012.

* cited by examiner

*Primary Examiner* — Susanna Moore
(74) *Attorney, Agent, or Firm* — Gary D. Greenblatt

(57) ABSTRACT

Disclosed are imidazopyridazinyl compounds of Formula (I): (I), or pharmaceutically salts and prodrugs thereof, wherein $R^3$ is $C_{2-4}$alkenyl or a cyclic group, and $R^1$ and $R^2$ are defined herein. Also disclosed are methods of using such compounds in the treatment of at least one CYP17 associated condition, such as, for example, cancer, and pharmaceutical compositions comprising such compounds.

(I)

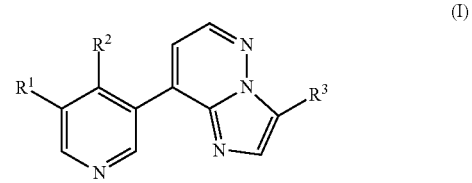

8 Claims, 1 Drawing Sheet

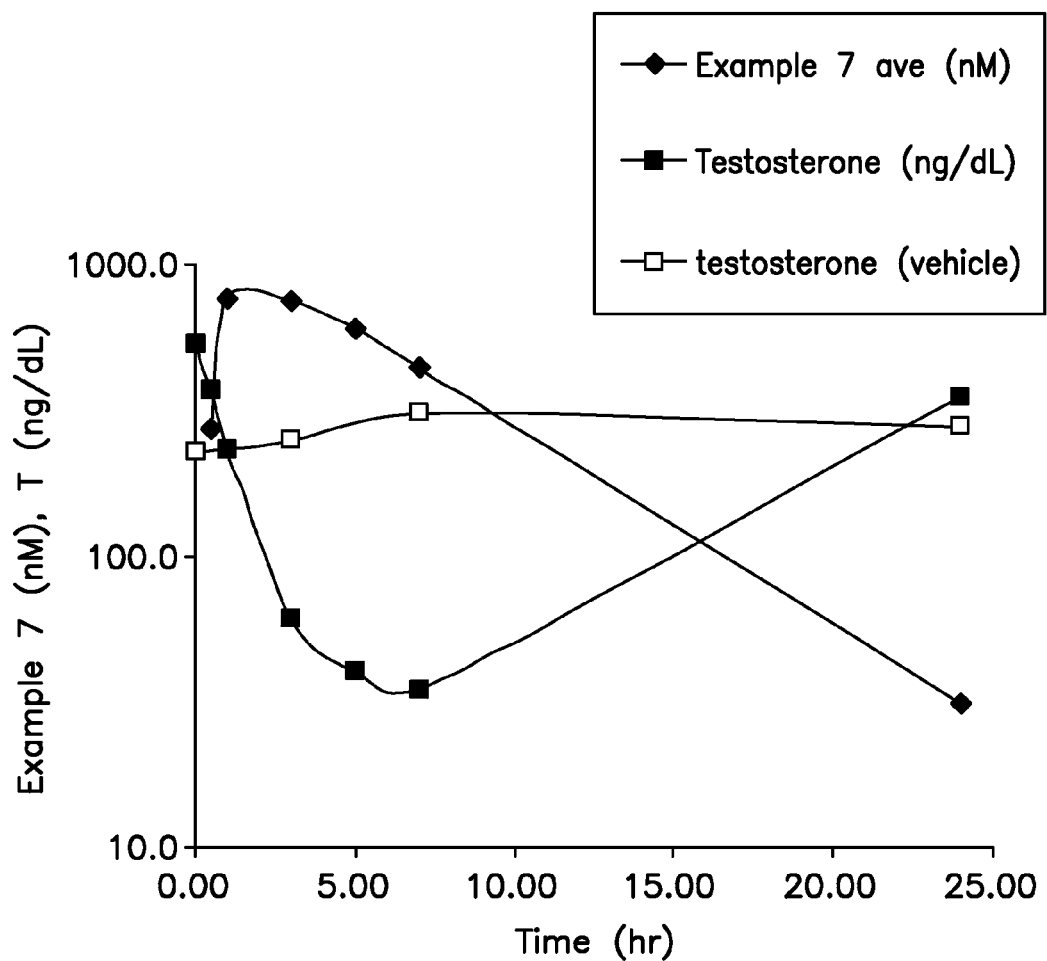

IMIDAZOPYRIDAZINYL COMPOUNDS

CROSS-REFERENCE TO RELATED APPLICATIONS

This application claims the benefit of U.S. Provisional Application Ser. No. 61/328,785 filed Apr. 28, 2010.

FIELD OF THE INVENTION

The present invention generally relates to imidazopyridazinyl compounds useful as CYP17 inhibitors. Provided herein are imidazopyridazinyl compounds, compositions comprising such compounds, and methods of their use. The invention further pertains to pharmaceutical compositions comprising at least one compound according to the invention that is useful for the treatment of conditions related to the CYP17 enzyme, such as cancer and other proliferative diseases.

BACKGROUND OF THE INVENTION

Prostate cancer is the second leading cause of cancer related mortality in American men. In 2007, there were 218,890 new cases with 27,000 deaths associated with prostate cancer. It is well known that androgens, such as testosterone and dihydrotestosterone, drive the growth of the prostate as well as prostate cancer at the level of the androgen receptor. The standard of care for advanced hormone sensitive prostate cancer involves surgical or chemical castration with a leutenizing releasing hormone agonist/antagonist to remove the androgens produced in the gonads from circulation. However, approximately 90% of androgens are produced in the testes with the remaining 10% being produced through the action of the adrenal gland. Thus, castration does not alleviate the action of all androgens. Further once a patient progresses to castration resistant prostate cancer, androgens are also produced at the level of the tumor, making treatment with anti-androgens more difficult.

The cytochrome P450 CYP17 is responsible for the biosynthesis of both dihydroepiandrostenedione and androstenedione which are precursors of both androgens and estrogen. Thus the production of all androgens and estrogens produced in the human body is mediated by CYP17. Blocking this enzyme would inhibit the production of gonadal, adrenal and tumoral androgens and could offer a new treatment option for prostate cancer and estrogen receptor-positive breast cancer patients.

Clinical proof-of-concept for CYP17 as a target for prostate cancer has been achieved with the antifungal ketoconazole and the steroidal CYP17 inhibitor abiraterone, which has progressed to Phase III clinical trials for prostate cancer.

There remains a need for compounds that are useful as inhibitors of CYP17 enzymes.

Applicants have found potent compounds that have activity as CYP17 inhibitors. These compounds are provided to be useful as pharmaceuticals with desired stability, bioavailability, therapeutic index, and toxicity values that are important to their drugability.

SUMMARY OF THE INVENTION

The present invention fills the foregoing need by providing imidazopyridazinyl compounds, which are useful as inhibitors of CYP17 enzymes, including salts and prodrugs thereof.

The present invention also provides pharmaceutical compositions comprising at pharmaceutically acceptable carrier; and at least one compound of Formula (I), or salts or prodrugs thereof.

The present invention also provides a method of treating a disease or disorder associated with the activity of the CYP17 enzyme, the method comprising administering to a mammalian patient a compound of Formula (I) or pharmaceutically acceptable salts or prodrugs thereof.

The present invention also provides processes and intermediates for making the compounds of Formula (I) or salts or prodrugs thereof.

The present invention also provides the compounds of Formula (I), or pharmaceutically acceptable salts or prodrugs thereof, for use in therapy.

The present invention also provides use of the compounds of Formula (I) or pharmaceutically acceptable salts or prodrugs thereof, for the manufacture of a medicament for the treatment of cancer.

The compounds of Formula (I) and compositions comprising the compounds are inhibitors of CYP17 enzymes, and may be used in treating, prevention, or curing various CYP17 enzyme related conditions. Pharmaceutical compositions comprising these compounds are useful in treating, preventing, or slowing the progression of diseases or disorders in a variety of therapeutic areas, such as cancer.

These and other features of the invention will be set forth in expanded form as the disclosure continues.

BRIEF DESCRIPTION OF THE DRAWINGS

The invention is illustrated by reference to the accompanying drawing described below.

FIG. 1 shows the plasma pharmacokinetics of Example 7 and testosterone in cynomolgus monkeys. Compound 7 was administered orally at 3 mg/kg. (♦) Example 7 (nM); (※) testosterone level for treatment with Example 7 (ng/dL); (○) testosterone level for treatment with vehicle only.

DETAILED DESCRIPTION OF THE INVENTION

The first aspect of the invention provides compounds of Formula (I):

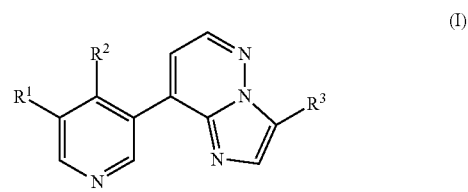

or pharmaceutically salts or prodrugs thereof; wherein:
$R^1$ is H, F, Cl, $C_{1-4}$alkyl, or $C_{1-4}$fluoroalkyl;
$R^2$ is H, halo, —CN, $C_{1-4}$alkyl, $C_{1-4}$fluoroalkyl, $C_{1-4}$alkoxy, $C_{1-4}$fluoroalkoxy, or —NR$^c$R$^c$;
or $R^1$ and $R^2$ can be combined to form a benzo fused radical substituted with zero, 1, or 2 R$^a$;
$R^3$ is $C_{2-4}$alkenyl or a cyclic group selected from $C_{3-6}$cycloalkyl, $C_{3-6}$cycloalkenyl, phenyl, naphthalenyl, or a 1- to 2-ring heteroaryl, wherein said cyclic group is substituted with zero to 3 R$^b$;
each R$^a$ is independently H, halo, —CN, $C_{1-4}$fluoroalkyl, $C_{1-4}$alkoxy, and/or $C_{1-4}$-fluoroalkoxy;
each R$^b$ is independently halo, $C_{1-4}$alkyl, $C_{1-4}$fluoroalkyl, $C_{1-4}$alkoxy, $C_{1-4}$fluoroalkoxy, —CN, $C_{1-4}$hydroxyalkyl, $C_{1-4}$thioalkyl, phenoxy, and/or —CH$_2$O(phenyl); and each $R^c$ is independently H, $C_{1-4}$alkyl, and/or $C_{3-6}$cycloalkyl, or both $R^c$ together with the nitrogen atom to which they are attached form a 5- or 6-membered heterocyclyl group.

In one embodiment, compounds of Formula (I) or pharmaceutically salts or prodrugs thereof are provided wherein $R^1$ is H, F, Cl, $C_{1-2}$alkyl, or $C_{1-2}$fluoroalkyl. Preferably $R^1$ is H, F, methyl, or —$CF_3$; and more preferably, $R^1$ is H.

In another embodiment, compounds of Formula (I) or pharmaceutically salts or prodrugs thereof are provided wherein $R^2$ is H, F, Cl, $C_{1-2}$alkyl, $C_{1-2}$fluoroalkyl, or $C_{1-2}$alkoxy. Preferably, $R^2$ is H, methyl, or —$OCH_3$; and more preferably, $R^2$ is methyl.

In a further embodiment, compounds of Formula (I) or pharmaceutically salts or prodrugs thereof are provided wherein $R^1$ and $R^2$ are combined to form a benzo fused radical substituted with zero, 1, or 2 $R^a$. These compounds have the structure of Formula (II):

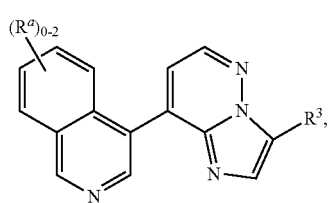

(II)

wherein each $R^a$ is independently H, halo, —CN, $C_{1-4}$alkyl, $C_{1-4}$fluoroalkyl, $C_{1-4}$alkoxy, and/or $C_{1-4}$fluoroalkoxy. Preferably, each $R^a$ is independently H, F, $C_{1-2}$alkyl, $C_{1-2}$fluoroalkyl, $C_{1-2}$alkoxy, and/or $C_{1-2}$fluoroalkoxy. More preferably, each $R^a$ is independently H, methyl, —$OCH_3$, $CF_3$, and/or —$OCF_3$.

In a further embodiment, compounds of Formula (I) or pharmaceutically salts or prodrugs thereof are provided wherein $R^3$ is $C_{2-4}$alkenyl. Preferably, $R^3$ is vinyl.

In a further embodiment, compounds of Formula (I) or pharmaceutically salts or prodrugs thereof are provided wherein $R^3$ is a cyclic group selected from $C_{3-6}$cycloalkyl, $C_{3-6}$cycloalkenyl, phenyl, naphthalenyl, and 1- to 2-ring heteroaryl, wherein said cyclic group is substituted with zero to 3 $R^b$.

In a further embodiment, compounds of Formula (I) or pharmaceutically salts or prodrugs thereof are provided wherein $R^3$ is a cyclic group selected from $C_{3-6}$cycloalkyl and $C_{3-6}$cycloalkenyl, wherein said cyclic group is substituted with zero to 3 $R^b$. Preferably, $R^3$ is cyclohexyl or cyclohexenyl, each substituted with zero to 3 $R^b$.

In a further embodiment, compounds of Formula (I) or pharmaceutically salts or prodrugs thereof are provided wherein $R^3$ is a cyclic group selected from phenyl, naphthalenyl, and 1- to 2-ring heteroaryl, wherein said cyclic group is substituted with zero to 3 $R^b$.

In a further embodiment, compounds of Formula (I) or pharmaceutically salts or prodrugs thereof are provided wherein $R^3$ is a cyclic group selected phenyl and naphthalenyl, wherein said cyclic group is substituted with zero to 3 $R^b$. Preferably, $R^3$ is phenyl substituted with zero to 3 $R^b$.

In a further embodiment, compounds of Formula (I) or pharmaceutically salts or prodrugs thereof are provided wherein $R^3$ is a cyclic group selected from 1- to 2-ring heteroaryl, wherein said cyclic group is substituted with zero to 3 $R^b$. Preferably, $R^3$ is a 1-ring heteroaryl. More preferably, $R^3$ is a 5- to 6-membered heteroaryl ring, including, for example, thiophenyl, thiazolyl, pyridinyl, pyrazinyl, and pyrimidinyl.

In a further embodiment, compounds of Formula (I) or pharmaceutically salts or prodrugs thereof are provided wherein $R^3$ is a cyclic group selected from 5- to 6-membered heteroaryl groups. The present embodiment includes compounds of Formula (I) wherein $R^3$ is thiophenyl, thiazolyl, pyrazinyl, or pyrimidinyl. The present embodiment includes compounds of Formula (I) wherein $R^3$ is a 5-membered heteroaryl ring.

In a further embodiment, compounds of Formula (I) or pharmaceutically salts or prodrugs thereof are provided wherein $R^3$ is a cyclic group selected from $C_{3-6}$cycloalkyl, $C_{3-6}$cycloalkenyl, phenyl, naphthalenyl, and 1- to 2-ring heteroaryl, wherein said cyclic group is substituted with zero to 3 $R^b$; and each $R^b$ is independently F, Cl, $C_{1-2}$alkyl, $C_{1-2}$fluoroalkoxy, $C_{1-2}$alkoxy, $C_{1-2}$fluoroalkoxy, —CN, $C_{1-2}$hydroxyalkyl, $C_{1-2}$thioalkyl, phenoxy, and/or —$CH_2O$(phenyl). Preferably, each $R^b$ is independently —$CH_3$, —$CF_3$, —$OCH_3$, —$OCF_3$, F, Cl, —$SCH_3$, —$CH_2OH$, phenoxy, and/or —$CH_2O$(phenyl).

In a further embodiment, compounds of Formula (I) or pharmaceutically salts or prodrugs thereof are provided wherein: $R^1$ is H; $R^2$ is H, —$CH_3$, or —$OCH_3$; or $R^1$ and $R^2$ can be combined to form a benzo fused radical; $R^3$ is: vinyl, cyclohexenyl, phenyl, naphthalenyl, thiophenyl, thiazolyl, pyridinyl, pyrazinyl, or pyrimidinyl, each substituted with zero to 3 $R^b$; and each $R^b$ is independently —$CH_3$, —$CF_3$, —$OCH_3$, —$OCF_3$, F, Cl, —$SCH_3$, —$CH_2OH$, phenoxy, and/or —$CH_2O$(phenyl).

In a further embodiment, compounds of Formula (I) or pharmaceutically salts or prodrugs thereof are provided wherein: $R^1$ is H; $R^2$ is H, —$CH_3$, or —$OCH_3$; or $R^1$ and $R^2$ can be combined to form a benzo fused radical; $R^3$ is phenyl, naphthalenyl, thiophenyl, thiazolyl, pyridinyl, pyrazinyl, or pyrimidinyl, each substituted with zero to 3 $R^b$; and each $R^b$ is independently —$CH_3$, —$CF_3$, —$OCH_3$, —$OCF_3$, F, Cl, —$SCH_3$, —$CH_2OH$, phenoxy, and/or —$CH_2O$(phenyl).

One embodiment provides compounds of Formula (I) or pharmaceutically acceptable salts or drugs thereof, wherein said compound is selected from: 8-(4-methylpyridin-3-yl)-3-phenylimidazo[1,2-b]pyridazine (1); 3,8-bis(4-methylpyridin-3-yl)imidazo[1,2-b]pyridazine (2); 3-(2-methoxyphenyl)-8-(4-methylpyridin-3-yl)imidazo[1,2-b]pyridazine (3); 8-(4-methylpyridin-3-yl)-3-(pyrimidin-5-yl)imidazo[1,2-b]pyridazine (4); 3-(2-fluorophenyl)-8-(4-methylpyridin-3-yl) imidazo[1,2-b]pyridazine (5); 3-(3-fluorophenyl)-8-(4-methylpyridin-3-yl)imidazo[1,2-b]pyridazine (6); 3-(4-fluorophenyl)-8-(4-methylpyridin-3-yl)imidazo[1,2-b] pyridazine (7); 3-(3-methoxyphenyl)-8-(4-methylpyridin-3-yl)imidazo[1,2-b]pyridazine (8); 8-(4-methylpyridin-3-yl)-3-m-tolylimidazo[1,2-b]pyridazine (9); 8-(4-methylpyridin-3-yl)-3-o-tolylimidazo[1,2-b]pyridazine (10); 3-(3-chlorophenyl)-8-(4-methylpyridin-3-yl)imidazo[1,2-b] pyridazine (11); 3-(2-chlorophenyl)-8-(4-methylpyridin-3-yl)imidazo[1,2-b]pyridazine (12); 3-cyclohexenyl-8-(4-methylpyridin-3-yl)imidazo[1,2-b]pyridazine (13); 3-(2-chloro-4-fluorophenyl)-8-(4-methylpyridin-3-yl)imidazo[1,2-b]pyridazine (14); 3-(2,4-difluorophenyl)-8-(4-methylpyridin-3-yl)imidazo[1,2-b]pyridazine (15); 3-(4-fluoro-2-(trifluoromethyl)phenyl)-8-(4-methylpyridin-3-yl) imidazo[1,2-b]pyridazine (16); 8-(4-methylpyridin-3-yl)-3-(2,4,5-trifluorophenyl)imidazo[1,2-b]pyridazine (17); 8-(4-methylpyridin-3-yl)-3-(pyrazin-2-yl)imidazo[1,2-b] pyridazine (18); 2-(8-(4-methylpyridin-3-yl)imidazo[1,2-b] pyridazin-3-yl)thiazole (19); 5-(8-(4-methylpyridin-3-yl)

imidazo[1,2-b]pyridazin-3-yl)thiazole (20); 8-(4-methylpyridin-3-yl)-3-(pyridin-2-yl)imidazo[1,2-b]pyridazine (21); 8-(4-methylpyridin-3-yl)-3-vinylimidazo[1,2-b]pyridazine (22); 3-phenyl-8-(pyridin-3-yl)imidazo[1,2-b]pyridazine (23); 3-(4-fluoro-2-methylphenyl)-8-(pyridin-3-yl)imidazo[1,2-b]pyridazine (24); 3-(4-fluoro-2-methoxyphenyl)-8-(pyridin-3-yl)imidazo[1,2-b]pyridazine (25); 3-(4-fluorophenyl)-8-(pyridin-3-yl)imidazo[1,2-b]pyridazine (26); 3-(2-chloro-4-fluorophenyl)-8-(pyridin-3-yl)imidazo[1,2-b]pyridazine (27); 4-(3-(2-chloro-4-fluorophenyl)imidazo[1,2-b]pyridazin-8-yl)isoquinoline (28); 4-(3-(2-(trifluoromethyl)pyridin-3-yl)imidazo[1,2-b]pyridazin-8-yl)isoquinoline (29); 4-(3-(4-fluorophenyl)imidazo[1,2-b]pyridazin-8-yl)isoquinoline (30); 3-(2,4-dichlorophenyl)-8-(4-methylpyridin-3-yl)imidazo[1,2-b]pyridazine (31); 8-(4-methylpyridin-3-yl)-3-(naphthalen-1-yl)imidazo[1,2-b]pyridazine (32); 3-(4-chlorophenyl)-8-(4-methylpyridin-3-yl)imidazo[1,2-b]pyridazine (33); 3-(3,5-dichlorophenyl)-8-(4-methylpyridin-3-yl)imidazo[1,2-b]pyridazine (34); 8-(4-methylpyridin-3-yl)-3-(thiophen-2-yl)imidazo[1,2-b]pyridazine (35); 8-(4-methylpyridin-3-yl)-3-(thiophen-3-yl)imidazo[1,2-b]pyridazine (36); 8-(4-methylpyridin-3-yl)-3-(3-(trifluoromethyl)phenyl)imidazo[1,2-b]pyridazine (37); 3-(3,5-dimethylphenyl)-8-(4-methylpyridin-3-yl)imidazo[1,2-b]pyridazine (38); 8-(4-methylpyridin-3-yl)-3-(2-(trifluoromethyl)phenyl)imidazo[1,2-b]pyridazine (39); 8-(4-methylpyridin-3-yl)-3-(pyridin-3-yl)imidazo[1,2-b]pyridazine (40); 3-(3,4-difluorophenyl)-8-(4-methylpyridin-3-yl)imidazo[1,2-b]pyridazine (41); 8-(4-methylpyridin-3-yl)-3-(2-phenoxyphenyl)imidazo[1,2-b]pyridazine (42); 3-(3,4-dimethylphenyl)-8-(4-methylpyridin-3-yl)imidazo[1,2-b]pyridazine (43); 8-(4-methylpyridin-3-yl)-3-(3-(methylthio)phenyl)imidazo[1,2-b]pyridazine (44); 8-(4-methylpyridin-3-yl)-3-(3-(trifluoromethoxy)phenyl)imidazo[1,2-b]pyridazine (45); 8-(4-methylpyridin-3-yl)-3-(2-(trifluoromethoxy)phenyl)imidazo[1,2-b]pyridazine (46); 8-(4-methylpyridin-3-yl)-3-(2-(phenoxymethyl)phenyl)imidazo[1,2-b]pyridazine (47); 3-(2,5-dichlorophenyl)-8-(4-methylpyridin-3-yl)imidazo[1,2-b]pyridazine (48); 3-(2,3-dimethylphenyl)-8-(4-methylpyridin-3-yl)imidazo[1,2-b]pyridazine (49); 3-(2,5-dimethylphenyl)-8-(4-methylpyridin-3-yl)imidazo[1,2-b]pyridazine (50); (2-(8-(4-methylpyridin-3-yl)imidazo[1,2-b]pyridazin-3-yl)phenyl)methanol (51); 3-(3-fluoro-5-methoxyphenyl)-8-(4-methylpyridin-3-yl)imidazo[1,2-b]pyridazine (52); 3-(8-(4-methylpyridin-3-yl)imidazo[1,2-b]pyridazin-3-yl)benzenesulfonamide (53); and 3-(4-fluorophenyl)-8-(4-methoxypyridin-3-yl)imidazo[1,2-b]pyridazine (54).

DEFINITIONS

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The terms "halo" and "halogen," as used herein, refer to F, Cl, Br, or I.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-6}$alkyl" denotes straight and branched chain alkyl groups with one to six carbon atoms.

The term "alkenyl" as used herein, refers to both branched and straight-chain unsaturated aliphatic hydrocarbon groups, which have one or more double carbon-carbon double bonds that may occur at any stable point along the chain. The term "$C_{2-4}$alkenyl" is intended to include $C_2$, $C_3$, and $C_4$ alkenyl groups, which include, for example, vinyl and propylenyl.

The term "fluoroalkyl" as used herein is intended to include both branched and straight-chain saturated aliphatic hydrocarbon groups substituted with one or more fluorine atoms. For example, "$C_{1-4}$fluoroalkyl" is intended to include $C_1$, $C_2$, $C_3$, and $C_4$ alkyl groups substituted with one or more fluorine atoms. Representative examples of fluoroalkyl groups include, but are not limited to, —$CF_3$ and —$CH_2CF_3$.

The term "cycloalkyl," as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "$C_{3-6}$cycloalkyl" denotes cycloalkyl groups with three to six carbon atoms.

The term "cycloalkenyl" refers to a nonaromatic, partially unsaturated hydrocarbon group containing from 1 to 2 rings and 3 to 8 carbons per ring, which have one or more double carbon-carbon bonds that may occur in any stable point along the ring. The term "$C_{3-7}$cycloalkenyl" is intended to include $C_3$, $C_4$, $C_5$, and $C_6$ cycloalkenyl groups. Exemplary cycloalkenyl groups include, but are not limited to, cyclopropenyl, cyclobutenyl, cyclopentenyl, and cyclohexenyl. Branched cycloalkenyl groups such as 1-methylcyclopropenyl and 2-methylcyclopropenyl are included in the definition of "cycloalkenyl".

The term "alkoxy," as used herein, refers to an alkyl group attached to the parent molecular moiety through an oxygen atom, for example, methoxy group (—$OCH_3$).

"Fluoroalkoxy" and "—O(fluoroalkyl)" represent a fluoroalkyl group as defined above attached through an oxygen linkage (—O—). For example, "$C_{1-4}$fluoroalkoxy" is intended to include $C_1$, $C_2$, $C_3$, and $C_4$ fluoroalkoxy groups.

The term "alkylthio" refers to an alkyl bonded through a sulfur linkage (—S—). For example, the term "thioalkyl" includes the group —$S(C_{1-4}$alkyl).

The term "hydroxyalkyl" includes both branched and straight-chain saturated alkyl groups substituted with one or more hydroxyl groups. For example, "hydroxyalkyl" includes —$CH_2OH$, $CH_2CH_2OH$, and $C_{1-4}$hydroxyalkyl. "$C_{1-4}$hydroxyalkyl" is intended to include $C_1$, $C_2$, $C_3$, and $C_4$ alkyl groups substituted with one or more hydroxy groups.

The term "benzyl" as used herein, refers to a methyl group in which one of the hydrogen atoms is replaced by a phenyl group.

The term "phenoxy" as used herein, refers to a group having the structure:

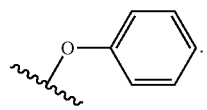

The term "heteroatom" refers to oxygen (O), sulfur (S), and nitrogen (N).

The term "thiophenyl" as used herein, refers to a group having the structure:

The term "heteroaryl" refers to substituted and unsubstituted aromatic 5- or 6-membered monocyclic groups and 9- or 10-membered bicyclic groups that have at least one heteroatom (O, S or N) in at least one of the rings, said heteroatom-containing ring preferably having 1, 2, or 3 heteroatoms independently selected from O, S, and/or N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups that are bicyclic must include at least one fully aromatic ring but the other fused ring may be aromatic or non-aromatic. The heteroaryl group may be attached at any available nitrogen or carbon atom of any ring. The heteroaryl ring system may contain zero, one, two or three substituents.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thiophenyl, oxadiazolyl, pyridinyl, pyrazinyl, pyrimidinyl, pyridazinyl, and triazinyl.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, and tetrahydroquinolinyl.

The term "heterocyclo" or "heterocyclyl" may be used interchangeably and refer to non-aromatic 3- to 7-membered monocyclic groups, in which the ring has 1 to 3 heteroatoms independently selected from O, S, and/or N. The heterocyclyl ring can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The heterocyclo group may be attached at any available nitrogen or carbon atom.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th Edition, Mack Publishing Company, Easton, Pa., p. 1418 (1985), the disclosure of which is hereby incorporated by reference.

Salt(s) of the Formula (I) compounds can be formed by, for example, reacting a Formula (I) compound with, for example, an equivalent amount of acid or base in a medium that allows the newly formed salt to, for example, either be precipitated out, or be isolated via lyophilization. Exemplary acidic salt(s) that the compounds of Formula (I) can form with inorganic and/or organic acids include, but are not limited to, for example, include acetate, ascorbate, benzoate, benzenesulfonate, bisulfate, bitartrate, acid citrate, citrate, ethanesulfonate, formate, fumarate, gentisinate, gluconate, glucaronate, glutamate, hydrochloride, hydrobromide, hydroiodide, isonicotinate, maleate, mesylate, methanesulfonate, nitrate, pantothenate, phosphate, acid phosphate, saccharate, salicylate, succinate, sulfate, tartrate, p-toluenesulfonate, trifluoroacetate, lactate, and pamoate [i.e., 1,1'-methylene-bis-(2-hydroxy-3-naphthoate)] salts. Such salts can be formed in accordance with methods known to a person of ordinary skill in the art.

Exemplary basic salt(s) that the compounds of Formula (I) can form with inorganic and/or organic bases include, but are not limited to, for example, ammonium salts; alkali metal salts, such as, for example, sodium, lithium and potassium salts: alkaline earth metal salts, such as, for example, calcium and magnesium salts; salts formed with organic bases, such as, for example, benzathines, dicyclohexylamines, 2-amino-2-(hydroxymethyl)propane-1,3-diol (trisamine or tris), hydrabamines (such as, for example, N,N-bis(dehydroabietyl)ethylenediamine), N-methyl-D-glucamines, N-methyl-D-glycamides, and t-butyl amines; salts formed with amino acids, such as, for example, arginine and lysine; and salts formed by using agents, such as, for example, lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), and aralkyl halides (e.g., benzyl and phenethyl bromides) to quaternize basic nitrogen-containing groups. Such salts can be formed in accordance with methods known to a person of ordinary skill in the art.

In addition, compounds of Formula (I) are, subsequent to their preparation, preferably isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

Any compound that can be converted in vivo to provide the bioactive agent (i.e., the compound of Formula (I)) is a prodrug within the scope and spirit of the invention.

The term "prodrugs" as employed herein includes esters and carbonates formed by reacting one or more hydroxyls of compounds of Formula (I) with alkyl, alkoxy, or aryl substituted acylating agents employing procedures known to those skilled in the art to generate acetates, pivalates, methylcarbonates, benzoates, and the like.

Various forms of prodrugs are well known in the art and are described in:
 a) Wermuth, C. G. et al., *The Practice of Medicinal Chemistry*, Chapter 31, Academic Press (1996);
 b) *Design of Prodrugs*, Bundgaard, H. ed., Elsevier (1985);
 c) Bundgaard, H., Chapter 5, "Design and Application of Prodrugs," *A Textbook of Drug Design and Development*, pp. 113-191, Krosgaard-Larsen, P. et al., eds., Harwood Academic Publishers (1991); and
 d) Testa, B. et al., *Hydrolysis in Drug and Prodrug Metabolism*, Wiley-VCH (2003).

In addition, compounds of the Formula (I) are, subsequent to their preparation, preferably isolated and purified to obtain a composition containing an amount by weight equal to or greater than 99% Formula (I) compound ("substantially pure" compound I), which is then used or formulated as described herein. Such "substantially pure" compounds of the Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an antagonist of CYP17 enzyme, or effective to treat cancer.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Compounds of the present invention may contain one or more additional asymmetric carbon atoms and therefore exist in two or more stereoisomeric forms. The present invention includes all of the possible individual stereoisomers, the individual tautomeric forms thereof, together with mixtures thereof. Separation of diastereoisomers may be achieved by conventional techniques, e.g., by fractional crystallization, chromatography or HPLC of a stereoisomeric mixture of a compound of the present invention, or a suitable salt or derivative thereof. An individual enantiomer of the compound may also be prepared from a corresponding optically pure intermediate or by resolution, such as by HPLC of the corresponding racemate using a suitable chiral support or by fractional crystallization of the diastereoisomeric salts formed by reaction of the corresponding racemate with a suitable optically active acid or base, as appropriate. All stereoisomers of the compounds of the instant invention are contemplated, either in admixture or in pure or substantially pure form.

The compounds of the present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Also embraced within this invention is a class of pharmaceutical compositions comprising the compound of Formula (I) or a pharmaceutically acceptable salt thereof in association with one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g., magnesium stearate and a disintegrating agent such as crospovidone. The carrier mixture may be filled into a gelatin capsule or compressed as a tablet.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension, or liquid. The pharmaceutical composition is preferably made in the form of a dosage unit containing a particular amount of the active ingredient. Examples of such dosage units are tablets or capsules. For example, these may contain an amount of active ingredient from about 0.5 to 2000 mg, preferably from about 0.5 to 500 mg, more preferably from about 0.5 to 150 mg. A suitable daily dose for a human or other mammal may vary widely depending on the condition of the patient and other factors, but, once again, can be determined using routine methods.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.01 to 1500 mg/kg body weight, preferably between about 0.5 and about 50 mg/kg body weight and most preferably between about 0.1 to 20 mg/kg body weight, may be appropriate. The daily dose can be administered in one to four doses per day.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinyl alcohol, and/or polyvinylpyrrolidone, and then tableted or encapsulated for convenient administration. Such capsules or tablets may contain a controlled-release formulation as may be provided in a dispersion of active compound in hydroxypropylmethyl cellulose.

The oily phase of the emulsions comprising compounds of Formula (I) may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e., CAPTISOL®), cosolvent solubilization (i.e., propylene glycol) or micellar solubilization (i.e., Tween 80).

The sterile injectable preparation may also be a sterile injectable solution or suspension in a non-toxic parenterally acceptable diluent or solvent, for example as a solution in propylene glycol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

The pharmaceutical compositions may be subjected to conventional pharmaceutical operations such as sterilization and/or may contain conventional adjuvants, such as preservatives, stabilizers, wetting agents, emulsifiers, and buffers. Tablets and pills can additionally be prepared with enteric coatings. Such compositions may also comprise adjuvants, such as wetting, sweetening, flavoring, and perfuming agents.

Pharmaceutical compositions of this invention comprise the compound of Formula (I), or a pharmaceutically acceptable salt thereof, and optionally an additional agent selected from any pharmaceutically acceptable carrier, adjuvant, and vehicle. Alternate compositions of this invention comprise a compound of the Formula (I) described herein, or a pharmaceutically acceptable salt thereof, and a pharmaceutically acceptable carrier, adjuvant, or vehicle.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

Utility

The compounds of Formula (I) are useful for the treatment of cancer, for example, cancers dependent upon androgen receptor signaling. These compounds inhibit the activity of the CYP17 enzyme, which is involved in biosynthesis of androgens. Blocking this enzyme would inhibit the production of gonadal, adrenal and tumoral androgens and offers a new treatment option for cancers dependent upon androgen receptor signaling, such as prostate cancer and estrogen receptor-positive breast cancer patients. Thus, the treatment comprises administering to the patient a compound of Formula (I) or a pharmaceutically acceptable salt thereof.

In one embodiment, a method is provided for treating cancer comprising administering compound of Formula (I) to a mammal in need thereof. The method of this embodiment can be used to treat a variety of cancers, including, but not limited to, bladder cancer, breast cancer, colorectal cancer, gastric cancer, head and neck cancer, kidney cancer, liver cancer, lung cancer, ovarian cancer, pancreas/gallbladder cancer, prostate cancer, thyroid cancer, osteosarcoma, rhabdomyosarcoma, malignant fibrous histiocytoma (MFH), fibrosarcoma, glioblastomas/astrocytomas, melanoma, and mesothelioma. Preferably, the method of this embodiment is used to treat prostate cancer. In one method of this embodiment, compound of Formula (I) is administered in a therapeutically effective amount.

In one embodiment, provided are methods for treating cancer in a patient wherein the cancer is dependent upon CYP17 activation, comprising administering to the patient in need thereof a therapeutically effective amount of a compound of Formula (I). In one method of this embodiment, a compound of Formula (I) is administered to treat prostate cancer. In another method of this embodiment, a compound of Formula (I) is administered to treat breast cancer. Preferably, a therapeutically effective amount of Compound (I) is administered.

The amount of a compound of Formula (I) which is administered and the dosage regimen for treating a particular cancer depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg body weight, preferably between about 0.5 and about 50 mg/kg body weight and most preferably between about 0.1 to 20 mg/kg body weight, may be appropriate may be appropriate. The daily dose can be administered in one to four doses per day.

In treating cancer, a combination of chemotherapeutic agents and/or other treatments (e.g., radiation therapy) is often advantageous. The second (or third) agent may have the same or different mechanism of action than the primary therapeutic agent. It may be especially useful to employ cytotoxic drug combinations wherein the two or more drugs being administered act in different manners or in different phased of the cell cycle, and/or where the two or more drugs have overlapping toxicities or side effects, and/or where the drugs being combined each has a demonstrated efficacy in treating the particular disease state manifested by the patient.

Accordingly, a compound of Formula (I) may be administered in combination with other anti-cancer treatments useful in the treatment of cancer or other proliferative diseases. The invention herein further comprises use of a compound of Formula (I) in preparing medicaments for the treatment of cancer, and/or it comprises the packaging of a compound of Formula (I) herein together with instructions that the compound be used in combination with other anti-cancer or cytotoxic agents and treatments for the treatment of cancer. The present invention further comprises combinations of a compound of Formula (I) and one or more additional agents in kit form, e.g., where they are packaged together or placed in separate packages to be sold together as a kit, or where they are packaged to be formulated together.

The compound of Formula (I) can be formulated or co-administered with other therapeutic agents that are selected for their particular usefulness in addressing side effects associated with the aforementioned conditions. For example, the compound of Formula (I) may be formulated with agents to prevent nausea, hypersensitivity and gastric irritation, such as antiemetics, and $H_1$ and $H_2$ antihistaminics.

The phrase "anti-cancer treatment" includes but is not limited to, for example, radiation therapy and surgery.

The other anti-cancer agents may be selected from any one or more of the following: alkylating agents (including nitrogen mustards, alkyl sulfonates, nitrosoureas, ethylenimine derivatives, and triazenes); anti-angiogenics (including matrix metalloproteinase inhibitors); antimetabolites (including adenosine deaminase inhibitors, folic acid antagonists, purine analogues, and pyrimidine analogues); antibiotics or antibodies (including monoclonal antibodies, CTLA-4 antibodies, anthracyclines); aromatase inhibitors; cell-cycle response modifiers; enzymes; farnesyl-protein transferase inhibitors; hormonal and antihormonal agents and steroids (including synthetic analogs, glucocorticoids, estrogens/anti-estrogens [e.g., SERMs], androgens/anti-androgens, progestins, progesterone receptor agonists, and luteinizing hormone-releasing [LHRH] agonists and antagonists); insulin-like growth factor (IGF)/insulin-like growth factor receptor (IGFR) system modulators (including IGFR1 inhibitors); integrin-signaling inhibitors; kinase inhibitors (including multi-kinase inhibitors and/or inhibitors of Src kinase or Src/abl, cyclin dependent kinase [CDK] inhibitors, panHer, Her-1 and Her-2 antibodies, VEGF inhibitors, including anti-VEGF antibodies, EGFR inhibitors, mitogen-activated protein [MAP] inhibitors, MEK inhibitors, Aurora kinase inhibitors, PDGF inhibitors, and other tyrosine kinase inhibitors or serine/threonine kinase inhibitors; microtubule-disruptor agents, such as ecteinascidins or their analogs and derivatives; microtubule-stabilizing agents such as taxanes, and the naturally-occurring epothilones and their synthetic and semi-synthetic analogs; microtubule-binding, destabilizing agents (including vinca alkaloids); topoisomerase inhibitors; prenyl-protein transferase inhibitors; platinum coordination complexes; signal transduction inhibitors; and other agents used as anti-cancer and cytotoxic agents such as biological response modifiers, growth factors, and immune modulators.

The above other therapeutic agents, when employed in combination with a compound of Formula (I), can be used, for example, in those amounts indicated in the Physicians' Desk Reference (PDR) or as otherwise determined by one of ordinary skill in the art.

In another embodiment, a compound of Formula (I) or a pharmaceutically acceptable salt thereof is used to treat prostate cancer.

In one embodiment, the patient is an animal.

In another embodiment, the patient is a mammalian species including, but not limited to, for example, humans and domestic animals, such as, for example, dogs, cats, and horses.

In one embodiment, the present invention provides a compound of Formula (I) or a pharmaceutically acceptable salt thereof for use in therapy.

In one embodiment, the use of a compound of Formula (I) or a pharmaceutically acceptable salt thereof in the manufacture of a medicament for the treatment of cancer, including prostate cancer, is provided.

Methods of Preparation

Preparation of compounds of general formula (I) is shown in Schemes 1 and 2 below. In one preparation, 3,8-dibromo-6-chloroimidazo[1,2-b]pyridazine (III) can be coupled to a 3-pyridylboronic acid/ester of general formula II via standard Suzuki conditions, well known to one skilled in the art, to give compounds of general formula IV. A second Suzuki coupling can then be done under similar conditions to yield compounds of general formula V. Dechlorination can be accomplished by many methods known to one skilled in the art including ammonium formate and Pd/C to give a compound of general formula (I).

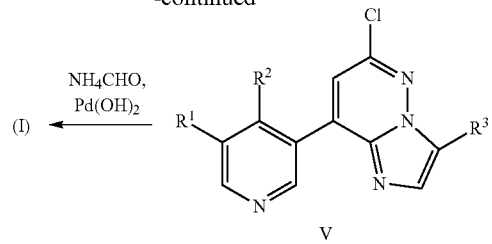

In another preparation, the 4-bromo-6-chloropyridazin-3-amine (VI) can be treated with aqueous 2-chloroacetaldehyde to yield 8-bromo-6-chloroimidazo[1,2-b]pyridazine (VII). Coupling of VII and a 3-pyridylboronic acid/ester of general formula II under standard Suzuki conditions can give compounds of general formula VIII. Dechlorination of compounds of general formula VIII can be accomplished by treatment with ammonium formate and Pd/C followed by iodination at the 3-position by treatment with a source of cationic iodine such as N-iodosuccinimide to give a compound of general structure IX. Standard Suzuki coupling of the iodide IX and a boronic acid/ester will then give a compound of general formula (I).

Scheme 2

In yet another preparation, 3-iodo-8-bromo-6-chloroimidazo[1,2-b]pyridazine can be prepared from 8-bromo-6-chloroimidazo[1,2-b]pyridazine (VI) by treatment with a source of cationic iodine such as N-iodosunnimide. The resultant 3-iodo-8-bromo-6-chloroimidazo[1,2-b]pyridazine can be subjected to Suzuki reaction with appropriate boronic acid to give general formula XI. A second Suzuki coupling can then be done under similar conditions to yield compounds of general formula V. Dechlorination can be accomplished by many methods known to one skilled in the art including ammonium formate and Pd/C to give a compound of general formula (I).

Scheme 1

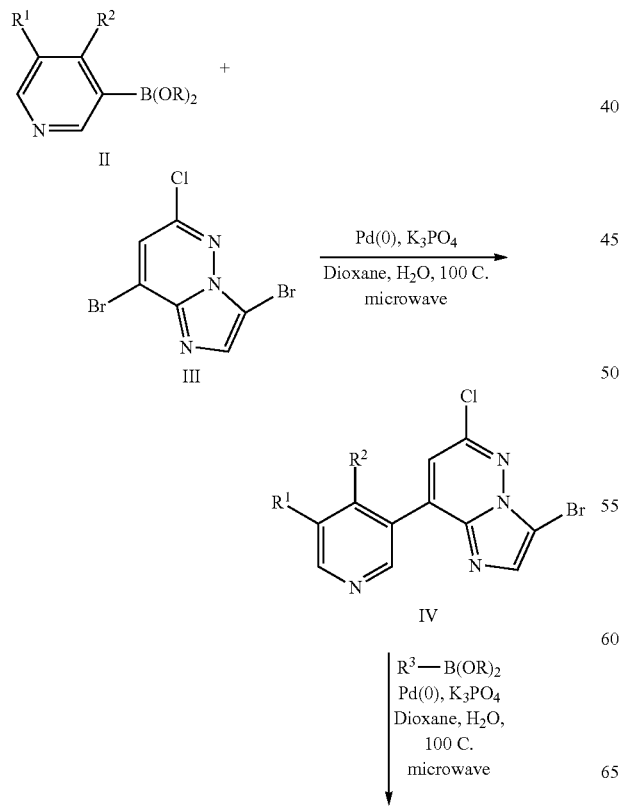

Scheme 3

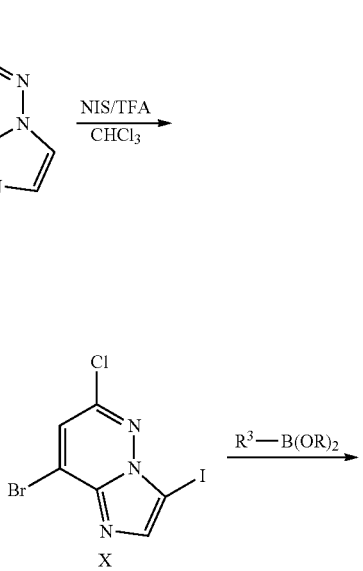

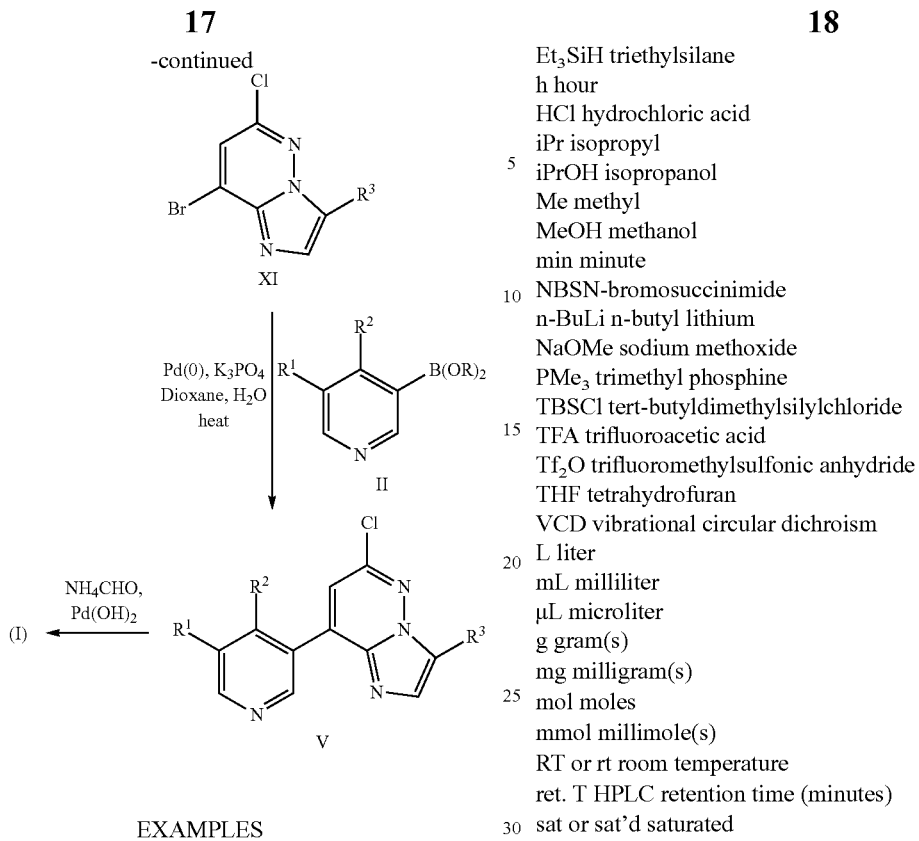

EXAMPLES

The present invention is further defined in the following examples. It should be understood that these examples are given by way of illustration only. From the above discussion and this example, one skilled in the art can ascertain the essential characteristics of this invention, and without departing from the spirit and scope thereof, can make various changes and modifications to the invention to adapt the invention to various uses and conditions. As a result, the present invention is not limited by the illustrative examples set forth herein below, but rather defined by the claims appended hereto.

All temperatures are in degrees Celsius (° C.) unless indicated otherwise herein.

All reactions were carried out with continuous magnetic stirring under an atmosphere of dry nitrogen. All evaporations and concentrations were carried out on a rotary evaporator under reduced pressure. Commercial reagents were used as received without additional purification. Solvents were commercial anhydrous grades and were used without further drying or purification. Flash chromatography was performed using silica gel (EMerck Kieselgel 60, 0.040-0.060 mm).

ABBREVIATIONS

AcOH acetic acid
Ac$_2$O acetic anhydride
CH$_2$Cl$_2$ dichloromethane
DMAP dimethylaminopyridine
DIEA diisopropylethylamine
DMF dimethylformamide
DMSO dimethylsulfoxide
Et ethyl
Et$_2$O diethyl ether
EtOAc ethyl acetate
EtOH ethanol
Et$_3$N triethyl amine
Et$_3$SiH triethylsilane
h hour
HCl hydrochloric acid
iPr isopropyl
iPrOH isopropanol
Me methyl
MeOH methanol
min minute
NBS N-bromosuccinimide
n-BuLi n-butyl lithium
NaOMe sodium methoxide
PMe$_3$ trimethyl phosphine
TBSCl tert-butyldimethylsilylchloride
TFA trifluoroacetic acid
Tf$_2$O trifluoromethylsulfonic anhydride
THF tetrahydrofuran
VCD vibrational circular dichroism
L liter
mL milliliter
µL microliter
g gram(s)
mg milligram(s)
mol moles
mmol millimole(s)
RT or rt room temperature
ret. T HPLC retention time (minutes)
sat or sat'd saturated
aq. aqueous
TLC thin layer chromatography
HPLC high performance liquid chromatography
Prep HPLC preparative reverse phase HPLC
LC/MS liquid chromatography/mass spectrometry
MS mass spectrometry
NMR nuclear magnetic resonance
mp melting point All final products were characterized by $^1$H NMR, HPLC, electrospray ionization (ESI MS) or atmospheric pressure ionization (API MS) mass spectrometry. $^1$H NMR spectra were obtained on either a 500 MHz JEOL or a 400 MHz Bruker instrument. $^{13}$C NMR spectra were recorded at 100 or 125 MHz. Field strengths are expressed in units of (parts per million, ppm) relative to the solvent peaks, and peak multiplicities are designated as follows: s, singlet; d, doublet; dd, doublet of doublets; dm, doublet of multiplets; t, triplet; q, quartet; br s, broad singlet; m, multiplet.

LC/MS and retention time:

Condition A: PHENOMENEX® Luna 3.0×50 mm S10 column, 4 min gradient time, flow rate: 4 mL/min; Solvent A: 10% MeOH/90% water/0.1% TFA; Solvent B: 10% water/90% MeOH/0.1% TFA.

Analytical HPLC Condition B: Analytical HPLC Method B: Waters Sunfire C18, 4.6×150 mm 3.5 µM (low pH), 0% B-100% B with flow rate 1 ml/min and gradient time 25 mM, Solvent A: 10% MeOH/90% water/0.1% TFA; Solvent B: 90% MeOH/10% water/0.1% TFA.

Analytical HPLC Condition C: water Xbridge phenyl, 4.6×150 mm 3 µM (low pH), 0% B-100% B with flow rate 1 ml/min and gradient time 25 min, Solvent A: 10% MeOH/90% water/0.1% TFA; Solvent B: 90% MeOH/10% water/0.1% TFA.

Condition D: SUPELCO® Ascentis Express 4.6×50 mm 2.7 µM C18, 4 min gradient time, flow rate: 4 mL/min; Sol-

Example 1

8-(4-Methylpyridin-3-yl)-3-phenylimidazo[1,2-b]pyridazine (1)

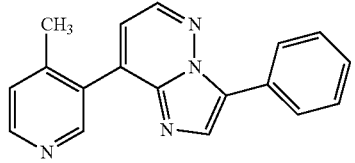

1A. 3-Bromo-6-chloro-8-(4-methylpyridin-3-yl)imidazo[1,2-b]pyridazine (IA)

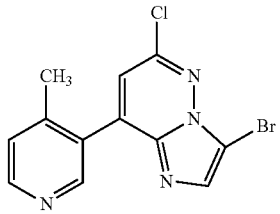

A microwave vial was charged with a mixture of 3,8-dibromo-6-chloroimidazo[1,2-b]pyridazine (1.0 g, 3.21 mmol), 4-methylpyridin-3-ylboronic acid (0.440 g, 3.21 mmol), tetrakis(triphenylphosphine)palladium(0) (0.371 g, 0.321 mmol), dioxane (16 mL), and $K_3PO_4$ (4.82 mL, 9.64 mmol) (2.0 M solution in water) was stirred at room temperature for 5 min. under nitrogen. The resulting mixture was heated to 100° C. for 4 h in a microwave heater. The reaction mixture was cooled to room temperature, quenched with water, and diluted with EtOAc. The layers were separated and the aqueous layer was extracted with EtOAc (3×20 mL). The combined organic layers were washed with brine, dried over anhydrous $Na_2SO_4$, and filtered. The filtrate was concentrated under reduced pressure. The residue was purified by BIOTAGE® (20-80% $EtOAc/CH_2Cl_2$, 1.5 L, then 20%-65% $B/CH_2Cl_2$ (0.9 L); B: 10% $MeOH/CH_2Cl_2$) to give 320 mg (15.4%) product. $^1$H NMR (400 MHz, $CD_3OD$) δ ppm 8.91 (1H, s), 8.82 (1H, d, J=5.79 Hz), 8.04 (1H, d, J=5.79 Hz), 7.88 (1H, s), 7.57 (1H, s), 2.54 (3H, s). LC (Conditions B & C): >95% purity; LC/MS: $R_t$=1.47 min. LC/MS (Condition A): 322.96/324.96.

1B. 6-Chloro-8-(4-methylpyridin-3-yl)-3-phenylimidazo[1,2-b]pyridazine (1B)

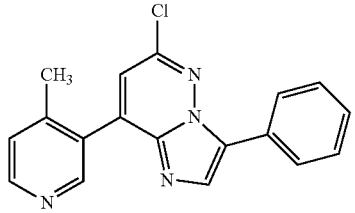

A microwave vial was charged with a mixture of 3-bromo-6-chloro-8-(4-methylpyridin-3-yl)imidazo[1,2-b]pyridazine (64 mg, 0.198 mmol), phenylboronic acid (24.12 mg, 0.198 mmol), tetrakis(triphenylphosphine)palladium(0) (22.86 mg, 0.020 mmol), dioxane (4 mL), and $K_3PO_4$ (0.297 mL, 0.593 mmol) (2.0 M water solution) was stirred at room temperature for 5 min. under nitrogen. The resulting mixture was heated to 100° C. for 8 h in microwave. The reaction mixture was cooled to room temperature, quenched with water, and diluted with EtOAc. The layers were separated and the aqueous layer was extracted with EtOAc (3×20 mL). The combined organic layers were washed with brine, dried over anhydrous $Na_2SO_4$, and filtered. The filtrate was concentrated under reduced pressure. The residue was purified by prep. HPLC to give 38 mg (44.3%) of the product. LC/MS: $R_t$=2.36 min. LC/MS (Condition A): 321.09/323.10.

Example 1

To a solution of 6-chloro-8-(4-methylpyridin-3-yl)-3-phenylimidazo[1,2-b]pyridazine, TFA salt (32 mg, 0.074 mmol) in EtOH (6 mL) in a vial were added ammonium formate (18.56 mg, 0.294 mmol) and palladium hydroxide on carbon (51.7 mg, 0.037 mmol) (20% wet). The vial was capped and heated to 70° C. for 2 h in an oil bath and cooled to room temperature. The reaction mixture was passed through a pad of CELITE® and washed with MeOH. The filtrate was concentrated and the residue was purified by prep. HPLC to give 24.8 mg (83%) product. $^1$H NMR (400 MHz, $CD_3OD$) δ ppm 8.90 (1H, s), 8.79 (2H, dd, J=11.46, 5.16 Hz), 8.20 (1H, s), 8.14 (2H, dd, J=8.44, 1.38 Hz), 8.02 (1H, d, J=5.79 Hz), 7.53 (2H, t, J=7.68 Hz), 7.32-7.48 (2H, m), 2.53 (3H, s); LC (Conditions B & C): >95% purity. LC/MS: $R_t$=1.83 min. LC/MS (Condition A): 287.12.

Example 2

3,8-bis(4-Methylpyridin-3-yl)imidazo[1,2-b]pyridazine (2)

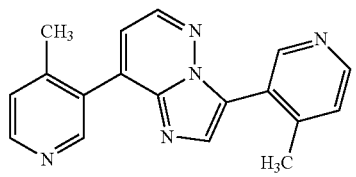

2A. 6-Chloro-3,8-bis(4-methylpyridin-3-yl)imidazo[1,2-b]pyridazine (2A)

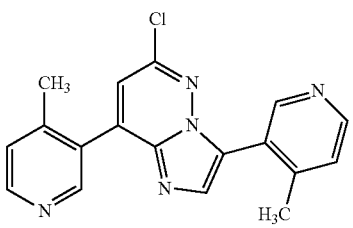

A microwave vial was charged with a mixture of 3,8-dibromo-6-chloroimidazo[1,2-b]pyridazine (210 mg, 0.674 mmol), 4-methylpyridin-3-ylboronic acid (184 mg, 1.35 mmol), tetrakis(triphenylphosphine)palladium(0) (78 mg, 0.067 mmol), dioxane (6 mL), and K$_3$PO$_4$ (1 mL, 2.023 mmol) was stirred at room temperature for 5 min. under nitrogen. The resulting mixture was heated to 100° C. for 8 h in microwave. The reaction mixture was cooled to room temperature, quenched with water, and diluted with EtOAc. The layers were separated and the aqueous layer was extracted with EtOAc (3×20 mL). The combined organic layers were washed with brine, dried over anhydrous Na$_2$SO$_4$, and filtered. The filtrate was concentrated under reduced pressure. The residue was purified by prep. HPLC to give 56 mg (24%) product. $^1$H NMR (400 MHz, CD$_3$OD) δ ppm 9.06 (1H, s), 8.93 (1H, s), 8.81 (2H, dd, J=15.23, 5.92 Hz), 8.17 (1H, s), 7.96-8.13 (2H, m), 7.68 (1H, s), 2.65 (3H, s), 2.58 (3H, s); LC/MS: R$_t$=0.88 min. LC/MS (Condition A): 336.14/338.15.

Example 2

A round bottom flask was charged with a mixture of 6-chloro-3,8-bis(4-methylpyridin-3-yl)imidazo[1,2-b]pyridazine (23 mg, 0.068 mmol), ammonium formate (25.9 mg, 0.411 mmol), and palladium hydroxide on carbon (19.24 mg, 0.014 mmol) (20% wet), and ethanol (5 mL) was stirred at room temperature for 5 min. under nitrogen. The reaction mixture was heated to 70° C. in an oil bath for 2 h and cooled to room temperature. The reaction mixture was passed through a pad of CELITE® and washed with MeOH. The filtrate was concentrated and the residue was purified by prep. HPLC to give 28.8 mg (78%) product. $^1$H NMR (400 MHz, CD$_3$OD) δ ppm 9.11 (1H, s), 8.95 (1H, s), 8.76-8.90 (2H, m), 8.74 (1H, d, J=4.78 Hz), 8.18 (1H, s), 8.08 (2H, dd, J=10.70, 5.92 Hz), 7.54 (1H, d, J=4.53 Hz), 2.66 (3H, s), 2.57 (3H, s); LC (Conditions B & C): >95% purity. LC/MS: R$_t$=0.39 min. LC/MS (Condition A): 302.17.

Example 3

3-(2-Methoxyphenyl)-8-(4-methylpyridin-3-yl)imidazo[1,2-b]pyridazine

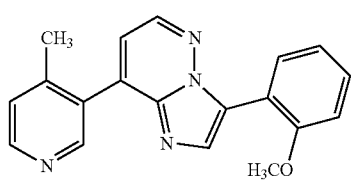

(3)

3A. 4-Bromo-6-chloropyridazin-3-amine

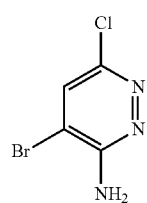

(3A)

A suspension of 6-chloropyridazin-3-amine (10.2 g, 48.9 mmol) in MeOH (200 mL) was sonicated for 10 min. Sodium bicarbonate (12.97 g, 154 mmol) was added followed by slow addition of bromine (4.77 mL, 93 mmol). The reaction mixture was stirred at room temperature over night and concentrated. The residue was diluted with EtOAc and the solid was filtered. The filtrate was washed with water and brine, dried over Na$_2$SO$_4$, and filtered. The filtrate was concentrated to give 10.2 g crude product as a brown solid which was used for the next step without further purification. $^1$H NMR (400 MHz, CD$_3$OD) δ ppm 7.93 (1H, s); LC/MS: R$_t$=0.75 min. LC/MS (Condition A): 208.04/210.04.

3B. 8-Bromo-6-chloroimidazo[1,2-b]pyridazine

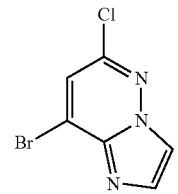

(3B)

To a solution of 4-bromo-6-chloropyridazin-3-amine (6.0 g, 28.8 mmol) was added 2-chloroacetaldehyde (22.60 g, 144 mmol) (50% water solution). The reaction mixture was heated to 50° C. overnight. The reaction mixture was cooled to room temperature and concentrated. The residue was diluted with CH$_2$Cl$_2$. Then, saturated NaHCO$_3$ was added slowly until bubbling ceased. The layers were separated. The aqueous layer was extracted with CH$_2$Cl$_2$ (3×30 mL). The combined organic layer was washed with water and brine, dried over Na$_2$SO$_4$. The crude product was purified by BIOTAGE® (10-40% EtOAc/CH$_2$Cl$_2$, 2.1 L) to give 4.1 g (61%) product as a brown solid. $^1$H NMR (400 MHz, CDCl$_3$) δ ppm 8.01 (1H, s), 7.84 (1H, s), 7.39 (1H, s); $^{13}$C NMR (101 MHz, CDCl$_3$) δ ppm 145.92 (1 C, s), 136.93 (1 C, s), 134.77 (1 C, s), 124.20 (1 C, s), 121.22 (1 C, s), 118.81 (1 C, s).

3C. 6-Chloro-8-(4-methylpyridin-3-yl)imidazo[1,2-b]pyridazine

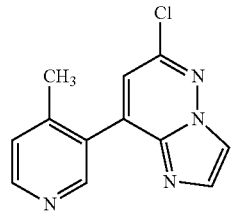

(3C)

A microwave vial was charged with a mixture of 8-bromo-6-chloroimidazo[1,2-b]pyridazine (1.1 g, 4.73 mmol), 4-methylpyridin-3-ylboronic acid (0.648 g, 4.73 mmol), tetrakis(triphenylphosphine)palladium(0) (0.547 g, 0.473 mmol), dioxane (14 mL), and K$_3$PO$_4$ (7.10 mL, 14.20 mmol) (2.0 M water solution) was stirred at room temperature for 5 min. under nitrogen. The resulting mixture was heated to 100° C. for 8 h in microwave. The reaction mixture was cooled to room temperature, quenched with water, and diluted with EtOAc. The layers were separated and the aqueous layer was extracted with EtOAc (3×20 mL). The combined organic layer was washed with brine, dried over anhydrous Na$_2$SO$_4$, and filtered. The filtrate was concentrated under reduced pressure. The residue was purified by BIOTAGE® (20-80% EtOAc/CH$_2$Cl$_2$, 1.5 L, then 20%-65% B/CH$_2$Cl$_2$, 0.9 L; B: 10% MeOH/CH$_2$Cl$_2$) to give 400 mg (34%) product. $^1$H NMR (400 MHz, CD$_3$OD) δ ppm 9.00 (1H, s), 8.80 (1H, d, J=5.79 Hz), 8.38 (1H, d, J=1.51 Hz), 8.04 (1H, d, J=6.04 Hz), 7.96 (1H, d, J=1.51 Hz), 7.86 (1H, s), 2.73 (3H, s); LC/MS: $R_t$=0.98 min. LC/MS (Condition A): 245.11/247.08.

3D.
8-(4-Methylpyridin-3-yl)imidazo[1,2-b]pyridazine (3D)

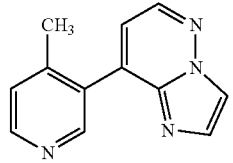

To a suspension of 6-chloro-8-(4-methylpyridin-3-yl)imidazo[1,2-b]pyridazine (800 mg, 3.27 mmol) in ethanol (80 mL) were added ammonium formate (825 mg, 13.08 mmol) and palladium hydroxide on carbon (459 mg, 0.327 mmol) (20% wet) under nitrogen. The suspension was heated to 70° C. in a sealed pressure bottle for 2 h and cooled to room temperature. The reaction mixture was passed through a pad of CELITE® and washed with MeOH. The filtrate was concentrated and the residue was used for the next step without further purification. $^1$H NMR (400 MHz, CDCl$_3$) δ ppm 8.53-8.67 (2H, m), 8.43 (1H, d, J=4.53 Hz), 8.09 (1H, d, J=1.26 Hz), 7.81 (1H, d, J=1.01 Hz), 7.31 (1H, d, J=5.04 Hz), 6.99 (1H, d, J=4.53 Hz), 2.33 (3H, s); LC/MS: $R_t$=0.21 min. LC/MS (Condition A): 211.18.

3E. 3-Iodo-8-(4-methylpyridin-3-yl)imidazo[1,2-b]pyridazine (3E)

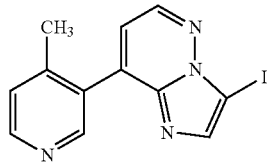

To a solution of 8-(4-methylpyridin-3-yl)imidazo[1,2-b]pyridazine, (480 mg, 1.48 mmol) in CHCl$_3$ (15 mL) were added N-iodo succinimide (400 mg, 1.776 mmol) and TFA (0.34 g, 2.96 mmol). The reaction mixture was stirred at room temperature for 2 h. The reaction mixture was quenched with saturated NaHCO$_3$ and extracted with CH$_2$Cl$_2$. The combined organic layer was washed with water and brine, and dried over Na$_2$SO$_4$. The crude product was purified by BIOTAGE® (20-40% EtOAc/CH$_2$Cl$_2$; 1.2 L). $^1$H NMR (400 MHz, CDCl$_3$) δ ppm 8.50-8.70 (3H, m), 7.90 (1H, s), 7.22-7.39 (4H, m), 7.06 (1H, d, J=4.53 Hz), 2.32 (3H, s); LC/MS: $R_t$=1.13 min. LC/MS (Condition A): 336.97.

Example 3

A microwave vial was charged with a mixture of 3-iodo-8-(4-methylpyridin-3-yl)imidazo[1,2-b]pyridazine (40 mg, 0.119 mmol), 3-methoxyphenylboronic acid (27.1 mg, 0.179 mmol), tetrakis(triphenylphosphine)palladium(0) (13.75 mg, 0.012 mmol), dioxane (2 mL), and K$_3$PO$_4$ (0.179 mL, 0.357 mmol) (2.0 M water solution) was stirred at room temperature for 5 min. under nitrogen. The resulting mixture was heated to 100° C. for 8 h in microwave. The reaction mixture was cooled to room temperature, quenched with water, and diluted with EtOAc. The layers were separated and the aqueous layer was extracted with EtOAc (3×20 mL). The combined organic layer was washed with brine, dried over anhydrous Na$_2$SO$_4$, and filtered. The filtrate was concentrated under reduced pressure. The residue was purified by prep. HPLC give 33.4 mg (62%) product.

$^1$H NMR (400 MHz, CD$_3$OD) δ ppm 9.00 (1H, s), 8.80 (1H, d, J=5.79 Hz), 8.38 (1H, d, J=1.51 Hz), 8.04 (1H, d, J=6.04 Hz), 7.96 (1H, d, J=1.51 Hz), 7.86 (1H, s), 2.73 (3H, s); LC (Conditions B & C): >95% purity. LC/MS: $R_t$=1.93 min. LC/MS (Condition A): 317.15.

Examples 4 to 17

Examples 4 to 17 are outlined in Table 1 and were prepared using procedures that are described above in Example 3.

TABLE 1

| Ex. | R³ | Compound Name | LC/MS* $R_t$ (min.) | (M + H)⁺ |
|---|---|---|---|---|
| 4 | pyrimidin-5-yl | 8-(4-methylpyridin-3-yl)-3-(pyrimidin-5-yl)imidazo[1,2-b]pyridazine | 1.01 | 289.12 |
| 5 | 2-fluorophenyl | 3-(2-fluorophenyl)-8-(4-methylpyridin-3-yl)imidazo[1,2-b]pyridazine | 1.70 | 305.14 |
| 6 | 3-fluorophenyl | 3-(3-fluorophenyl)-8-(4-methylpyridin-3-yl)imidazo[1,2-b]pyridazine | 2.23 | 305.14 |

TABLE 1-continued

| Ex. | R³ | Compound Name | LC/MS* R$_t$ (min.) | (M + H)⁺ |
|---|---|---|---|---|
| 7 | 4-fluorophenyl | 3-(4-fluorophenyl)-8-(4-methylpyridin-3-yl)imidazo[1,2-b]pyridazine | 1.84 | 305.14 |
| 8 | 3-methoxyphenyl | 3-(3-methoxyphenyl)-8-(4-methylpyridin-3-yl)imidazo[1,2-b]pyridazine | 1.91 | 317.15 |
| 9 | 3-methylphenyl | 8-(4-methylpyridin-3-yl)-3-m-tolylimidazo[1,2-b]pyridazine | 2.05 | 301.20 |
| 10 | 2-methylphenyl | 8-(4-methylpyridin-3-yl)-3-o-tolylimidazo[1,2-b]pyridazine | 1.62 | 301.18 |
| 11 | 3-chlorophenyl | 3-(3-chlorophenyl)-8-(4-methylpyridin-3-yl)imidazo[1,2-b]pyridazine | 2.19 | 321.09/ 323.08 |
| 12 | 2-chlorophenyl | 3-(2-chlorophenyl)-8-(4-methylpyridin-3-yl)imidazo[1,2-b]pyridazine | 1.75 | 321.09/ 323.09 |
| 13 | cyclohexenyl | 3-cyclohexenyl-8-(4-methylpyridin-3-yl)imidazo[1,2-b]pyridazine | 2.06 | 291.19 |
| 14 | 2-chloro-4-fluorophenyl | 3-(2-chloro-4-fluorophenyl)-8-(4-methylpyridin-3-yl)imidazo[1,2-b]pyridazine | 2.03 | 339.06/ 341.05 |
| 15 | 2,4-difluorophenyl | 3-(2,4-difluorophenyl)-8-(4-methylpyridin-3-yl)imidazo[1,2-b]pyridazine | 1.89 | 323.10 |

TABLE 1-continued

| Ex. | R³ | Compound Name | LC/MS* R_t (min.) | (M + H)⁺ |
|---|---|---|---|---|
| 16 | (4-trifluoromethyl-4-fluorophenyl) | 3-(4-fluoro-2-(trifluoromethyl)phenyl)-8-(4-methylpyridin-3-yl)imidazo[1,2-b]pyridazine | 2.46 | 373.15 |
| 17 | (2,4,5-trifluorophenyl) | 8-(4-methylpyridin-3-yl)-3-(2,4,5-trifluorophenyl)imidazo[1,2-b]pyridazine | 2.11 | 341.12 |

*LC/MS: Condition A

Example 18

8-(4-Methylpyridin-3-yl)-3-(pyrazin-2-yl)imidazo[1,2-b]pyridazine (18)

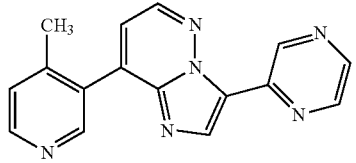

A microwave vial was charged with a mixture of 3-iodo-8-(4-methylpyridin-3-yl)imidazo[1,2-b]pyridazine, TFA (66 mg, 0.147 mmol), 2-(tributylstannyl)pyrazine (162 mg, 0.440 mmol), tetrakis(triphenylphosphine)palladium(0) (33.9 mg, 0.029 mmol), and dioxane (4 mL) was stirred at RT for 5 min. under nitrogen. The resulting mixture was heated to 114° C. for 15 h in microwave. The reaction mixture was cooled to room temperature and concentrated under reduced pressure. The residue was purified by prep. HPLC to give 18.2 mg (30%) product. ¹H NMR (400 MHz, CD₃OD) δ ppm 9.86 (1H, d, J=1.76 Hz), 8.97 (1H, s), 8.86 (2H, dd, J=16.12, 5.29 Hz), 8.66-8.79 (1H, m), 8.59 (1H, d, J=2.52 Hz), 8.56 (1H, s), 8.10 (1H, d, J=6.04 Hz), 7.54 (1H, d, J=4.78 Hz), 2.57 (3H, s); LC (Conditions B & C): >95% purity. LC/MS: R_t=1.05 min. LC/MS (Condition A): 289.12.

Examples 19 to 22

Examples 19 to 22 are outlined in Table 2 and were prepared using procedures that are described above in Example 18.

TABLE 2

| Ex. | R³ | Compound Name | HPLC Ret. Time (min.) Condition A | (M + H)⁺ |
|---|---|---|---|---|
| 19 | thiazol-2-yl | 2-(8-(4-methylpyridin-3-yl)imidazo[1,2-b]-pyridazin-3-yl)thiazole | 1.29 | 294.09 |
| 20 | thiazol-5-yl | 5-(8-(4-methylpyridin-3-yl)imidazo[1,2-b]-pyridazin-3-yl)thiazole | 1.09 | 294.09 |
| 21 | pyridin-2-yl | 8-(4-methylpyridin-3-yl)-3-(pyridin-2-yl)-imidazo[1,2-b]pyridazine | 0.45 | 288.21 |
| 22 | vinyl | 8-(4-methylpyridin-3-yl)-3-vinylimidazo[1,2-b]pyridazine | 1.12 | 237.16 |

Example 23

3-Phenyl-8-(pyridin-3-yl)imidazo[1,2-b]pyridazine

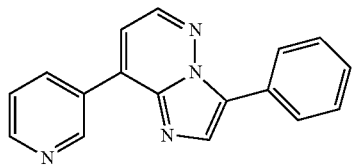

(23)

23A.
6-Chloro-8-(pyridin-3-yl)imidazo[1,2-b]pyridazine

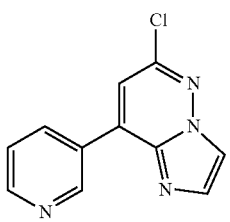

(23A)

A microwave vial was charged with a mixture of 8-bromo-6-chloroimidazo[1,2-b]pyridazine (1.06 g, 4.56 mmol), 3-(1,3,2-dioxaborinan-2-yl)pyridine (0.743 g, 4.56 mmol), dioxane (14 mL), and tetrakis(triphenylphosphine)palladium(0) (0.527 g, 0.456 mmol), and $K_3PO_4$ (2.90 g, 13.68 mmol) (2.0 M water solution) was stirred at room temperature for 5 min. under nitrogen. The resulting mixture was heated to 100° C. for 8 h in microwave. The reaction mixture was cooled to room temperature, quenched with water, and diluted with EtOAc. The layers were separated and the aqueous layer was extracted with EtOAc (3×20 mL). The combined organic layer was washed with brine, dried over anhydrous Na2SO4, and filtered. The filtrate was concentrated under reduced pressure. The residue was purified by BIOTAGE® (20-60% EtOAc/hex, 1.5 L) to the product (0.39 g, 37%). LC/MS: Rt=1.07 min. LC/MS (Condition A): 231.09/233.09.

23B. 8-(Pyridin-3-yl)imidazo[1,2-b]pyridazine

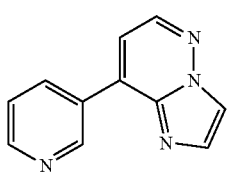

(23B)

To a suspension of 6-chloro-8-(pyridin-3-yl)imidazo[1,2-b]pyridazine (160 mg, 0.69 mmol) in EtOH (15 mL) was added ammonium formate (175 mg, 2.77 mmol) and palladium hydroxide on carbon (50 mg, 0.07 mmol) (20% wet) under nitrogen. The reaction mixture was heated to 50° C. for 20 min and cooled to room temperature. The reaction mixture was passed through a pad of CELITE® and washed with MeOH. The filtrate was concentrated and the residue was purified by BIOTAGE® (20-60% EtOAc/$CH_2Cl_2$, 1.5 L) to give the product (99 mg, 73%). LC (Condition B & C): >95% homogeneity index. LC/MS: $R_f$=0.31 min. LC/MS (Condition A): 197.21.

23C.
3-Iodo-8-(pyridin-3-yl)imidazo[1,2-b]pyridazine

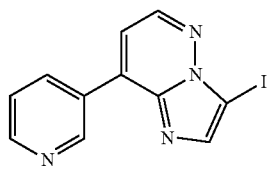

(23C)

To a solution of 8-(pyridin-3-yl)imidazo[1,2-b]pyridazine (490 mg, 2.497 mmol) in $CHCl_3$ (15 mL) was added N-iodo succinimide (618 mg, 2.75 mmol) in $CHCl_3$ (5 mL) dropwise at 0° C. The reaction mixture was stirred at room temperature for 1 h, quenched with saturated $NaHCO_3$, and extracted with $CH_2Cl_2$. The combined organic layer was washed with brine, dried over anhydrous $Na_2SO_4$, and filtered. The filtrate was concentrated under reduced pressure. The crude product was purified by BIOTAGE® (15-55% EtOAc/$CH_2Cl_2$, 1.2 L) to give the product (350 mg, 43%). LC/MS: Rt=1.23 min. LC/MS (Condition A): 323.00.

A microwave vial was charged with a mixture of 3-iodo-8-(pyridin-3-yl)imidazo[1,2-b]pyridazine (65 mg, 0.202 mmol), phenylboronic acid (61.5 mg, 0.504 mmol), tetrakis (triphenylphosphine)palladium(0) (46.6 mg, 0.040 mmol), dioxane (4 mL), and $K_3PO_4$ (130 mg, 0.65 mmol) (2.0 M water solution) was stirred at room temperature for 5 min. under nitrogen. The resulting mixture was heated to 100° C. for 8 h in microwave. The reaction mixture was cooled to room temperature, quenched with water, and diluted with EtOAc. The layers were separated and the aqueous layer was extracted with EtOAc (3×20 mL). The combined organic layer was washed with brine, dried over anhydrous $Na_2SO_4$, and filtered. The filtrate was concentrated under reduced pressure. The residue was purified by prep. HPLC to afford Example 26 (25.5 mg, 51%).

$^1$H NMR (400 MHz, $CD_3OD$) δ ppm 9.64 (1H, d, J=2.01 Hz), 9.05 (1H, dt, J=8.25, 1.79 Hz), 8.92 (1H, dd, J=5.54, 1.26 Hz), 8.74 (1H, d, J=4.53 Hz), 8.24 (1H, s), 7.98-8.17 (3H, m), 7.68 (1H, d, J=4.53 Hz), 7.38-7.60 (3H, m); LC (Conditions B & C): >95% purity. LC/MS: Rt=1.88 min. LC/MS (Condition A): 273.13.

Examples 24 to 27

Examples 24 to 27 are outlined in Table 3 and were prepared using the general procedure described above in Example 23.

TABLE 3

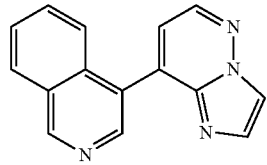

| Ex. | R³ | Compound Name | HPLC Ret. Time (min.) Condition A | (M + H)+ |
|---|---|---|---|---|
| 24 | 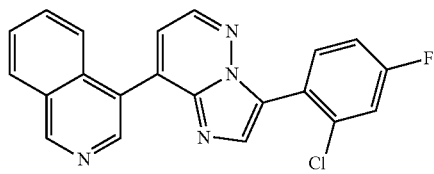 | 3-(4-fluoro-2-methylphenyl)-8-(pyridin-3-yl)-imidazo[1,2-b]pyridazine | 2.00 | 305.15 |
| 25 | | 3-(4-fluoro-2-methoxyphenyl)-8-(pyridin-3-yl)-imidazo[1,2-b]pyridazine | 1.95 | 321.17 |
| 26 | | 3-(4-fluoro-phenyl)-8-(pyridin-3-yl)-imidazo[1,2-b]pyridazine | 2.09 | 291.14 |
| 27 | | 3-(2-chloro-4-fluorophenyl)-8-(pyridin-3-yl)-imidazo[1,2-b]pyridazine | 2.19 | 325.11 |

Example 28

4-(3-(2-Chloro-4-fluorophenyl)imidazo[1,2-b]pyridazin-8-yl)isoquinoline (28)

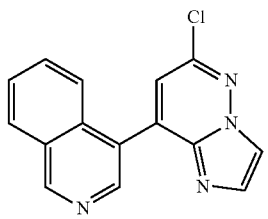

28A. 4-(6-Chloroimidazo[1,2-b]pyridazin-8-yl)isoquinoline (28A)

A microwave vial was charged with a mixture of 8-bromo-6-chloroimidazo[1,2-b]pyridazine (0.8 g, 3.44 mmol), isoquinolin-4-ylboronic acid (0.6 g, 1.734 mmol), dioxane (16 mL), tetrakis(triphenylphosphine)palladium(0) (0.100 g, 0.087 mmol), and $K_3PO_4$ (2.60 mL, 5.20 mmol) (2.0 M water solution) was stirred at room temperature for 5 min. under nitrogen. The resulting mixture was heated to 100° C. for 4 h in microwave. The reaction mixture was cooled to room temperature, quenched with water, and diluted with EtOAc. The layers were separated and the aqueous layer was extracted with EtOAc (3×20 mL). The combined organic layer was washed with brine, dried over anhydrous $Na_2SO_4$, and filtered. The filtrate was concentrated under reduced pressure. The residue was purified by BIOTAGE® (30-100% EtOAc/EtOAc/$CH_2Cl_2$, 1.2 L, then 50-100% B/EtOAc/$CH_2Cl_2$, B: 10% MeOH/EtOAc/$CH_2Cl_2$, 800 mL) to give the product (0.27 g, 55%). $^1$H NMR (400 MHz, $CDCl_3$) δ ppm 9.41 (1H, s), 8.72 (1H, s), 8.66 (1H, d, J=4.53 Hz), 8.03-8.17 (1H, m), 7.90 (1H, s), 7.71 (3H, d, J=3.02 Hz), 7.26 (1H, d, J=4.53 Hz); LC/MS: $R_t$=1.35 min. LC/MS (Condition A): 281.13/283.13.

28B. 4-(Imidazo[1,2-b]pyridazin-8-yl)isoquinoline (28B)

A pressure bottle charged with a mixture of 4-(6-chloroimidazo[1,2-b]pyridazin-8-yl)isoquinoline (270 mg, 0.962 mmol), ammonium formate (243 mg, 3.85 mmol), palladium hydroxide on carbon (67 mg, 0.1 mmol) (20% wet), and EtOH (5 ml). The pressure bottle charged with a mixture of 4-(6-chloroimidazo[1,2-b]pyridazin-8-yl)isoquinoline (270 mg, 0.962 mmol), ammonium formate (243 mg, 3.85 mmol), palladium hydroxide on carbon (67 mg, 0.1 mmol) (20% wet), and EtOH (5 ml) was stirred at room temperature for 5 min. under nitrogen. The resulting mixture was heated to 50° C. for 20 min and cooled to room temperature. The reaction mixture was passed through a pad of CELITE® and washed with MeOH. The filtrate was concentrated and the residue was purified by BIOTAGE® (20-60% EtOAc/$CH_2Cl_2$, 1.5 L) to give the product (220 mg, 93%). LC/MS: $R_t$=0.54 min. LC/MS (Condition A): 247.17.

28C. 4-(3-Iodoimidazo[1,2-b]pyridazin-8-yl)isoquinoline (28C)

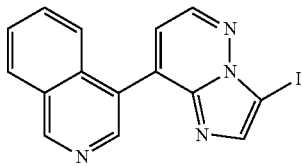

To a solution of 4-(imidazo[1,2-b]pyridazin-8-yl)isoquinoline (220 mg, 0.893 mmol) in $CHCl_3$ (10 mL) were added N-iodo succinimide (241 mg, 1.072 mmol) and TFA (0.275 mL, 3.57 mmol) In $CHCl_3$ (1 mL). The reaction mixture was stirred at room temperature for 2 h and quenched with saturated $NaHCO_3$. The layers were separated and the combined organic layer was washed with water and brine, dried over $Na_2SO_4$. The crude product was purified by BIOTAGE® (30-70% EtOAc/$CH_2Cl_2$, 0.8 L) to give the product (290 mg, 87%). ¹H NMR (400 MHz, CDCl₃) δ ppm 9.41 (1H, s), 8.72 (1H, s), 8.66 (1H, d, J=4.53 Hz), 8.07-8.17 (1H, m), 7.90 (1H, s), 7.71 (3H, d, J=3.02 Hz), 7.28 (3H, s), 7.26 (1H, d, J=4.53 Hz); LC/MS: R$_t$=1.53 min. LC/MS (Condition A): 373.08.

Example 28

A vial charged with a mixture of 4-(3-iodoimidazo[1,2-b]pyridazin-8-yl) isoquinoline (41 mg, 0.110 mmol), 4-fluorophenylboronic acid (18.50 mg, 0.132 mmol), PdCl₂ (dppf)-CH₂Cl₂ adduct (9.00 mg, 0.011 mmol), K₃PO₄ (70.2 mg, 0.331 mmol) (2.0M water solution), and dioxane (6 mL) was stirred at room temperature for 5 min. under nitrogen and capped. The resulting mixture was heated to 85° C. over night. The reaction mixture was cooled to room temperature, quenched with water, and diluted with EtOAc. The layers were separated and the aqueous layer was extracted with EtOAc (3×20 mL). The combined organic layer was washed with brine, dried over anhydrous Na₂SO₄, and filtered. The filtrate was concentrated under reduced pressure. The vial was capped and heated to 85° C. overnight. The residue was dissolved in MeOH/TFA and purified by prep. HPLC to give the product (29.6 mg, 77%). ¹H NMR (400 MHz, CD₃OD) δ ppm 9.85 (1H, s), 8.85 (1H, s), 8.80 (1H, d, J=4.53 Hz), 8.58 (1H, d, J=8.06 Hz), 7.93-8.17 (4H, m), 7.80 (1H, dd, J=8.56, 6.04 Hz), 7.67 (1H, d, J=4.53 Hz), 7.50 (1H, dd, J=8.56, 2.52 Hz), 7.30 (1H, td, J=8.44, 2.52 Hz); LC/MS: R$_t$=2.24 min. LC (Conditions B & C): >95% purity. LC/MS: R$_t$=2.35 min. LC/MS (Condition A): 375.16.

Examples 29 to 30

Examples 29 to 30 are outlined in Table 4 and were prepared according to the general procedure described in Example 28.

TABLE 4

| Ex. | R³ | Compound | HPLC Ret. Time (min.) Condition A | (M + H)⁺ |
|---|---|---|---|---|
| 29 | (3-(2-trifluoromethyl)pyridin-3-yl) | 4-(3-(2-(trifluoromethyl)pyridin-3-yl)imidazo[1,2-b]pyridazin-8-yl)isoquinoline | 2.44 | 392.16 |
| 30 | (4-fluorophenyl) | 4-(3-(4-fluorophenyl)imidazo[1,2-b]pyridazin-8-yl)isoquinoline | 2.24 | 341.17 |

Example 31 to 53

Examples 31 to 53 were prepared using the following general procedure: 3-iodo-8-(4-methylpyridin-3-yl)imidazo[1,2-b]pyridazine (943 mg) was dissolved in dioxane (28 mL) and added into 23 pre-weighed boronic acids in 16×100 mm Wheaton vial, and followed by adding K₃PO₄ (0.24 mL) into each vial. Then, Pd(Ph₃P)₄ (17 mg, 0.015 mmol) was added. The vial was flashed with argon and capped. The plates were heated at 85° C. in a shaker for 4 hours. The reactions were not complete as determined by LCMS analysis and was heated at 85° C. overnight. The samples were dried, dissolved in DMF, filtered, and purified using preparative HPLC.

TABLE 5

| Ex. | R³ | Compound | HPLC* Ret t (min.) | (M + H)⁺ |
|---|---|---|---|---|
| 31 | (2,4-dichlorophenyl) | 3-(2,4-dichlorophenyl)-8-(4-methylpyridin-3-yl)imidazo[1,2-b]pyridazine | 4.7 | 354.90 |
| 32 | (naphthalen-1-yl) | 8-(4-methylpyridin-3-yl)-3-(naphthalen-1-yl)imidazo[1,2-b]pyridazine | 4.41 | 336.98 |
| 33 | (4-chlorophenyl) | 3-(4-chlorophenyl)-8-(4-methylpyridin-3-yl)imidazo[1,2-b]pyridazine | 4.68 | 320.94 |

TABLE 5-continued

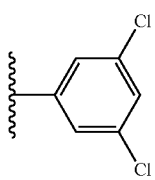 [SMILES: *c1cc(Cl)cc(Cl)c1]

| Ex. | R³ | Compound | HPLC* Ret t (min.) | (M + H)⁺ |
|---|---|---|---|---|
| 34 | 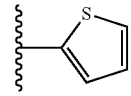 [SMILES: *c1cccs1] | 3-(3,5-dichlorophenyl)-8-(4-methylpyridin-3-yl)imidazo[1,2-b]pyridazine | 5.46 | 354.90 |
| 35 | 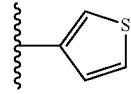 | 8-(4-methylpyridin-3-yl)-3-(thiophen-2-yl)imidazo[1,2-b]pyridazine | 3.95 | 292.95 |
| 36 | 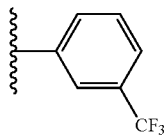 | 8-(4-methylpyridin-3-yl)-3-(thiophen-3-yl)imidazo[1,2-b]pyridazine | 3.96 | 292.94 |
| 37 | 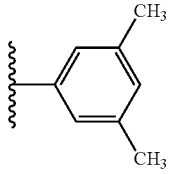 [SMILES: *c1cc(C)cc(C)c1] | 8-(4-methylpyridin-3-yl)-3-(3-(trifluoromethyl)phenyl)-imidazo[1,2-b]pyridazine | 4.8 | 354.93 |
| 38 | 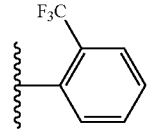 [SMILES: *c1ccccc1C(F)(F)F] | 3-(3,5-dimethylphenyl)-8-(4-methylpyridin-3-yl)imidazo[1,2-b]pyridazine | 4.77 | 315.01 |
| 39 | 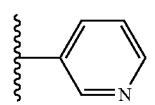 | 8-(4-methylpyridin-3-yl)-3-(2-(trifluoromethyl)phenyl)-imidazo[1,2-b]pyridazine | 4.14 | 354.96 |
| 40 | 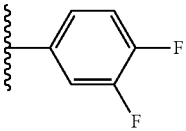 [SMILES: *c1ccc(F)c(F)c1] | 8-(4-methylpyridin-3-yl)-3-(pyridin-3-yl)imidazo[1,2-b]pyridazine | 2.75 | 288.00 |
| 41 |  | 3-(3,4-difluorophenyl)-8-(4-methylpyridin-3-yl)imidazo[1,2-b]pyridazine | 4.41 | 322.95 |

TABLE 5-continued

| Ex. | R³ | Compound | HPLC* Ret t (min.) | (M + H)⁺ |
|---|---|---|---|---|
| 42 | 2-phenoxyphenyl | 8-(4-methylpyridin-3-yl)-3-(2-phenoxyphenyl)imidazo[1,2-b]pyridazine | 4.82 | 378.96 |
| 43 | 3,4-dimethylphenyl | 3-(3,4-dimethylphenyl)-8-(4-methylpyridin-3-yl)imidazo[1,2-b]pyridazine | 4.83 | 315.01 |
| 44 | 3-(methylthio)phenyl | 8-(4-methylpyridin-3-yl)-3-(3-(methylthio)phenyl)imidazo[1,2-b]pyridazine | 4.51 | 332.96 |
| 45 | 3-(trifluoromethoxy)phenyl | 8-(4-methylpyridin-3-yl)-3-(3-(trifluoromethoxy)phenyl)imidazo[1,2-b]pyridazine | 5.00 | 370.93 |
| 46 | 2-(trifluoromethoxy)phenyl | 8-(4-methylpyridin-3-yl)-3-(2-(trifluoromethoxy)phenyl)imidazo[1,2-b]pyridazine | 4.42 | 370.92 |
| 47 | 2-(phenoxymethyl)phenyl | 8-(4-methylpyridin-3-yl)-3-(2-(phenoxymethyl)phenyl)imidazo[1,2-b]pyridazine | 4.91 | 392.98 |
| 48 | 2,5-dichlorophenyl | 3-(2,5-dichlorophenyl)-8-(4-methylpyridin-3-yl)imidazo[1,2-b]pyridazine | 4.68 | 354.91 |
| 49 | 2,3-dimethylphenyl | 3-(2,3-dimethylphenyl)-8-(4-methylpyridin-3-yl)imidazo[1,2-b]pyridazine | 4.39 | 315.01 |

TABLE 5-continued

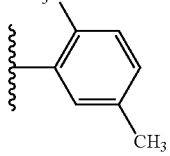

| Ex. | R³ | Compound | HPLC* Ret t (min.) | (M + H)⁺ |
|---|---|---|---|---|
| 50 | 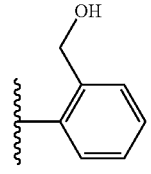 [SMILES: *c1ccccc1CO] | 3-(2,5-dimethylphenyl)-8-(4-methylpyridin-3-yl)imidazo[1,2-b]pyridazine | 4.38 | 315.01 |
| 51 | 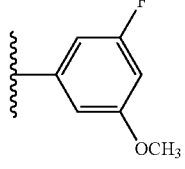 | (2-(8-(4-methylpyridin-3-yl)imidazo[1,2-b]pyridazin-3-yl)phenyl)methanol | 2.85 | 316.99 |
| 52 | 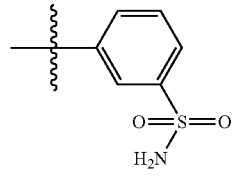 [SMILES: *c1cccc(S(N)(=O)=O)c1] | 3-(3-fluoro-5-methoxyphenyl)-8-(4-methylpyridin-3-yl)imidazo[1,2-b]pyridazine | 4.36 | 334.97 |
| 53 | 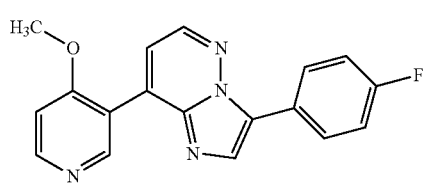 | 3-(8-(4-methylpyridin-3-yl)imidazo[1,2-b]pyridazin-3-yl)benzenesulfonamide | 1.79 | 366.09 |

*HPLC: Condition D

Example 54

3-(4-Fluorophenyl)-8-(4-methoxypyridin-3-yl)imidazo[1,2-b]pyridazine (54)

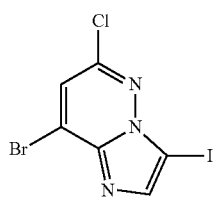

54A.
8-Bromo-6-chloro-3-iodoimidazo[1,2-b]pyridazine (54A)

To a solution of 8-bromo-6-chloroimidazo[1,2-b]pyridazine (1.2 g, 5.16 mmol) in chloroform (30 mL) were added NIS (1.161 g, 5.16 mmol) and TFA (0.795 mL, 10.32 mmol). The reaction mixture was stirred at room temperature for 2 h and quenched with NaHCO$_3$. The organic layers were washed with brine and dried over Na$_2$SO$_4$. The crude product was purified by BIOTAGE® (100% CH$_2$Cl$_2$) to give the product (1.4 g, 76%). $^1$H NMR (400 MHz, CDCl$_3$) δ ppm 7.91 (1H, s), 7.46 (1H, s); LC/MS: Rt=2.44 min. LC/MS (Condition A): 357.80/359.80/361.80.

54B. 8-Bromo-6-chloro-3-(4-fluorophenyl)imidazo[1,2-b]pyridazine

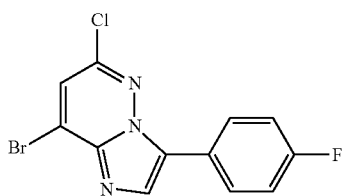

(54B)

A pressure bottle charged with a mixture of 8-bromo-6-chloro-3-iodoimidazo[1,2-b]pyridazine (1.4 g, 3.91 mmol), 4-fluorophenylboronic acid (0.558 g, 3.98 mmol), dioxane (20 mL), and tetrakis(triphenylphosphine)palladium(0) (0.452 g, 0.39 mmol), and K$_3$PO$_4$ (2.49 g, 11.72 mmol) (2.0 M water solution) was stirred at room temperature for 5 min. under nitrogen. The resulting mixture was heated to 85° C. for 8 h. The reaction mixture was cooled to room temperature, quenched with water, and diluted with EtOAc. The layers were separated and the aqueous layer was extracted with EtOAc (3×20 mL). The combined organic layer was washed with brine, dried over anhydrous Na$_2$SO$_4$, and filtered. The filtrate was concentrated under reduced pressure. The residue was purified by BIOTAGE® (0-20% EtOAc/CH$_2$Cl$_2$, 1.2 L) to give the product (0.56 g, 44%). LC/MS: Rt=3.22 min. LC/MS (Condition A): 325.83/327.83/329.83.

Example 54

A vial charged with a mixture of 8-bromo-6-chloro-3-(4-fluorophenyl)imidazo[1,2-b]pyridazine (150 mg, 0.459 mmol), 4-methoxypyridin-3-ylboronic acid, HCl salt (83 mg, 0.438 mmol), PdCl$_2$ (dppf)-CH$_2$Cl$_2$ Adduct (18.76 mg, 0.023 mmol), dioxane (2 mL), and K$_3$PO$_4$ (488 mg, 2.297 mmol). The contents of the vial were stirred at room temperature for 5 min. under nitrogen. The resulting mixture was heated to 95° C. for 15 h. The reaction mixture was cooled to room temperature, quenched with water, and diluted with EtOAc. The layers were separated and the aqueous layer was extracted with EtOAc (3×20 mL). The combined organic layer was washed with brine, dried over anhydrous Na$_2$SO$_4$, and filtered. The filtrate was concentrated under reduced pressure. The residue was purified prep. HPLC to give the product (35 mg, 11%). LC/MS: Rt=2.43 min. LC/MS (Condition A): 355.00/357.00.

To a suspension of 6-chloro-3-(4-fluorophenyl)-8-(4-methoxypyridin-3-yl)imidazo[1,2-b]pyridazine, 3 TFA (35 mg, 0.050 mmol), in EtOH (10 mL) was added ammonium formate (25 mg, 0.4 mmol) and palladium hydroxide on carbon (10 mg, 0.02 mmol) (20% wet) under nitrogen. The reaction mixture was heated to 50° C. for 20 min and cooled to room temperature. The reaction mixture was passed through a pad of CELITE® and washed with MeOH. The filtrate was concentrated and the residue was purified by prep. HPLC to give the product (12.1 mg, 72%). $^1$H NMR (400 MHz, CD$_3$OD) δ ppm 9.08 (1H, s), 8.88 (1H, dd, J=6.92, 1.13 Hz), 8.75 (1H, d, J=4.78 Hz), 8.20 (1H, s), 8.16 (2H, dd, J=8.94, 5.41 Hz), 7.84 (1H, d, J=7.05 Hz), 7.59 (1H, d, J=4.78 Hz), 7.27.

BIOLOGICAL ASSAYS

The pharmacological properties of the compounds of this invention may be confirmed by a number of biological assays. The exemplified biological assays, which follow, have been carried out with compounds of the invention and/or salts thereof.

CYP17 Total SPA assay

The assays were performed in U-bottom 384-well optiplates. The final assay volume was 15 µl prepared from 7.5 µl additions of microsomes (prepared as a high-speed pellet from homogenized HEK2 cells stably transfected with CYP17), substrates (3H-Pregnenolone and NADPH) and test compounds in assay buffer (50 mM Potassium phosphate pH 7.2, 10% glycerol). The reaction was initiated by the combination of the microsomes and substrates in wells containing compound. The reaction was incubated at room temperature for 45 minutes and terminated by adding 7.5 µl of 0.2N HCl to each well. Following an incubation period of 10 minutes, anti-DHEA-coated SPA beads were added to the terminated reaction. The plate was sealed and incubated overnight with shaking at 4° C. The beads were allowed to settle in the plate for 1 hour and the plate read on a TOPCOUNT® (Perkin-Elmer) plate reader.

Inhibition data were calculated by comparison to no enzyme control reactions for 100% inhibition and vehicle-only reactions for 0% inhibition. The final concentration of reagents in the assays are NADPH, 2 mM; 3H-Pregnenolone, 1 uM; microsomes, 1.25 ug/ml; Anti-DHEA-SPA beads (0.125 mg/well) in 0.5% Triton X-100 and DMSO, 0.05%. Dose response curves were generated to determine the concentration required inhibiting 50% of enzyme activity (IC$_{50}$). Compounds were dissolved at 10 mM in dimethylsulfoxide (DMSO) and evaluated at eleven concentrations, each in duplicate. IC$_{50}$ values were derived by non-linear regression analysis.

Table 5 below lists the IC$_{50}$ values for the following examples of this invention measured in the Total CYP17 SPA Assay hereinabove. The compounds of the present invention, as exemplified by the following examples, showed Human CYP17 SPA IC$_{50}$ values of less than 1 µM.

TABLE 5

| Human CYP17 Inhibition | |
|---|---|
| Ex. | Human CYP17 SPA IC$_{50}$ (nM) |
| 1 | 41 |
| 3 | 16 |
| 7 | 56 |
| 9 | 120 |
| 11 | 97 |
| 26 | 524 |
| 34 | 664 |
| 35 | 9 |
| 37 | 129 |
| 38 | 279 |

CYP17 Lyase Assay

Human CYP17 was expressed in HEK293 cells and microsomal preparations were made and subsequently used as the source of enzyme in the lyase assay. The reaction consists of 200 nM [3H]-Hydroxypregnenolone (ARC), 200 nM 17-Hydroxypregnenolone (Sigma), 2 mM NADPH (Cal-Biochem), and CYP17-HEK293 microsomes which were incubated in the presence of DMSO or test compounds for 20 minutes at room temperature. Compounds were dissolved in DMSO and serially diluted. The reaction was stopped by the addition of 0.2 N HCl and the product was captured using anti-mouse YSi SPA beads (GE) conjugated to an anti-DHEA monoclonal antibody (Abcam). Signal intensity determined by a Packard Top Count was used to calculate percent inhibition and $IC_{50}$ values.

Cyp17 Hydroxylase Assay

*E. coli* was transformed to express active human CYP17 and membranes prepared from the transformed *E. coli* were used as the source of enzyme. The reaction was carried out in a 50 uL final volume containing 200 nM hCYP17 membranes, 25 µM Pregnenolone (Sigma), 7 mM NADPH (Cal-Biochem), 1 µM cytochrome P450 reductase (Invitrogen), and 50 mM sodium phosphate buffer, pH 7.3. The $IC_{50}$ determination of compounds dissolved in 100% DMSO was done by serial dilution into the assay buffer to a final concentration of 0.2% DMSO. The reaction was incubated at 37° C. for 120 minutes and stopped by the addition of 200 uL of 0.02N HCl in acetonitrile. Samples were then spun at 750000 g and 200 uL of the supernatant was transferred to a clean tube for analysis. The product of the reaction, 17 alpha pregnenolone, was measured via LC/MS.

Cyp17 HEK293 Cell Based Assay

HEK293 cells were stably transfected with human Cyp17 and individual clones analyzed for Cyp17 enzymatic activity via LC/MS. A single clone showing robust activity was selected and scaled up. Cells were seeded in 96 well plates and a serial dilution of compounds dissolved in DMSO was added to the cells. Following an incubation of 4 hours, reactions were neutralized by the addition of 200 ul of acetonitrile containing 0.5 uM pregnenolone as tracer. Plates were spun down at 2K for 15 minutes and supernatants transferred to siliconized 96 well plates. The end product of the reaction DHEA was analyzed via LC/MS.

1-Day Cyno PK/PD Study Protocol

Animals: All procedures involving animals and their care were conducted in conformity with the guidelines that are in compliance with the Bristol-Myers Squibb Institutional Animal Care and Use Committee. Fully mature male cynomolgus monkeys (>4 yrs of age; 5-6 kg) were from an in-house colony. All the monkeys used had chronically implanted femoral vein access ports. For oral studies, all animals were fasted overnight prior to dosing and were fed 4 hr after dosing. All animals had free access to water and were conscious throughout the study.

Drug: For all oral pharmacokinetic studies in cynomolgus monkeys, the tested compound was formulated in polyethylene glycol (PEG 400): water (80:20, v:v) at concentrations of 1-5 mg/mL.

Drug Treatment: The tested compound was administered by oral gavage to cynomolgus monkeys.

Sampling: Blood samples were collected from the femoral port, at 15, 30, and 45 min, and 1, 2, 4, 6, 8, 12, 24, 30, and 48 hr after oral administration. All blood samples were collected into syringes containing sodium heparin. The plasma fraction was immediately separated by centrifugation (14,000 rpm, 10 min, 4° C.), frozen on dry ice, and stored at −20° C. until the samples were analyzed.

Analysis of Tested Compound: Plasma samples were thawed and treated with two volumes of acetonitrile containing internal standard. After centrifugation to remove precipitated proteins, an aliquot of supernatant was analyzed by LC/MS/MS.

Analysis of Steroids. Plasma samples were thawed, and assayed in accordance with package insert instructions for the following kits: Coat-A-Count total testosterone solid phase RIA kit, Coat-A-Count total progesterone solid phase RIA kit, and Coat-A-Count total cortisol solid phase RIA kit (Diagnostic Product Corp, Siemens Healthcare Diagnostics, Deerfield, Ill.).

FIG. 1 shows the results of a 1-day PK/PD study in NHP cynomolgus monkeys with Example 7. Example 7 was formulated in 80% PEG-400/water at a concentration of 1 mL/Kg and a dose of 3 mg/Kg. The formulation was then dosed orally at time=0 and blood samples were taken over a 24 hour period to monitor for drug exposure and testosterone levels. FIG. 1 shows that testosterone levels are reduced to ~15 ng/dL after single oral dose of Example 7, consistent with an inhibitor of CYP17 lyase. Also shown in FIG. 1 is the testosterone levels after oral dosing of the vehicle only (control).

The invention claimed is:

1. A compound of Formula (I)

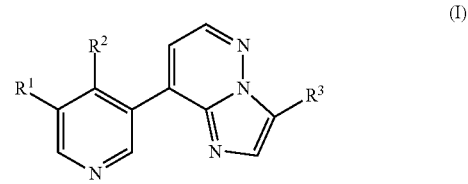

or a pharmaceutically salt thereof; wherein:

$R^1$ is H, F, Cl, $C_{1-4}$alkyl, or $C_{1-4}$fluoroalkyl;

$R^2$ is H, halo, —CN, $C_{1-4}$alkyl, $C_{1-4}$fluoroalkyl, $C_{1-4}$alkoxy, $C_{1-4}$fluoroalkoxy, or —$NR^cR^c$;

or $R^1$ and $R^2$ can be combined to form a benzo fused radical substituted with zero, 1, or 2 $R^a$;

$R^3$ is $C_{2-4}$alkenyl or a cyclic group selected from $C_{3-6}$cycloalkyl, $C_{3-6}$cycloalkenyl, phenyl, naphthalenyl, or a 1- to 2-ring heteroaryl, wherein said cyclic group is substituted with zero to 3 $R^b$;

each $R^a$ is independently H, halo, —CN, $C_{1-4}$alkyl, $C_{1-4}$fluoroalkyl, $C_{1-4}$alkoxy, and/or $C_{1-4}$-fluoroalkoxy;

each $R^b$ is independently halo, $C_{1-4}$alkyl, $C_{1-4}$fluoroalkyl, $C_{1-4}$alkoxy, $C_{1-4}$fluoroalkoxy, —CN, $C_{1-4}$hydroxyalkyl, $C_{1-4}$thioalkyl, phenoxy, and/or —$CH_2O$(phenyl); and each $R^c$ is independently H, $C_{1-4}$alkyl, and/or $C_{3-6}$cycloalkyl, or both $R^c$ together with the nitrogen atom to which they are attached form a 5- or 6-membered heterocyclyl group.

2. The compound according to claim 1 or a pharmaceutically acceptable salt thereof, wherein:

$R^1$ is H;

$R^2$ is H, —$CH_3$, or —$OCH_3$;

or $R^1$ and $R^2$ can be combined to form a benzo fused radical;

$R^3$ is:

a) vinyl;

b) cyclohexenyl;

c) phenyl, naphthalenyl, thiophenyl, thiazolyl, pyridinyl, pyrazinyl, or pyrimidinyl, each substituted with zero to 3 $R^b$;

and each $R^b$ is independently —CH$_3$, —CF$_3$, —OCH$_3$, —OCF$_3$, F, Cl, —SCH$_3$, —CH$_2$OH, phenoxy, and/or —CH$_2$O(phenyl).

3. The compound according to claim 2 or a pharmaceutically acceptable salt thereof, wherein:
$R^1$ is H;
$R^2$ is H, —CH$_3$, or —OCH$_3$;
or $R^1$ and $R^2$ can be combined to form a benzo fused radical;
$R^3$ is phenyl, naphthalenyl, thiophenyl, thiazolyl, pyridinyl, pyrazinyl, or pyrimidinyl, each substituted with zero to 3 $R^b$;
and each $R^b$ is independently —CH$_3$, —CF$_3$, —OCH$_3$, —OCF$_3$, F, Cl, —SCH$_3$, —CH$_2$OH, phenoxy, and/or —CH$_2$O(phenyl).

4. The compound according to claim 1 or a pharmaceutically acceptable salt thereof, wherein said compound is selected from: 8-(4-methylpyridin-3-yl)-3-phenylimidazo[1,2-b]pyridazine (1); 3,8-bis(4-methylpyridin-3-yl)imidazo[1,2-b]pyridazine (2); 3-(2-methoxyphenyl)-8-(4-methylpyridin-3-yl)imidazo[1,2-b]pyridazine (3); 8-(4-methylpyridin-3-yl)-3-(pyrimidin-5-yl)imidazo[1,2-b]pyridazine (4); 3-(2-fluorophenyl)-8-(4-methylpyridin-3-yl)imidazo[1,2-b]pyridazine (5); 3-(3-fluorophenyl)-8-(4-methylpyridin-3-yl)imidazo[1,2-b]pyridazine (6); 3-(4-fluorophenyl)-8-(4-methylpyridin-3-yl)imidazo[1,2-b]pyridazine (7); 3-(3-methoxyphenyl)-8-(4-methylpyridin-3-yl)imidazo[1,2-b]pyridazine (8); 8-(4-methylpyridin-3-yl)-3-m-tolylimidazo[1,2-b]pyridazine (9); 8-(4-methylpyridin-3-yl)-3-o-tolylimidazo[1,2-b]pyridazine (10); 3-(3-chlorophenyl)-8-(4-methylpyridin-3-yl)imidazo[1,2-b]pyridazine (11); 3-(2-chlorophenyl)-8-(4-methylpyridin-3-yl)imidazo[1,2-b]pyridazine (12); 3-cyclohexenyl-8-(4-methylpyridin-3-yl)imidazo[1,2-b]pyridazine (13); 3-(2-chloro-4-fluorophenyl)-8-(4-methylpyridin-3-yl)imidazo[1,2-b]pyridazine (14); 3-(2,4-difluorophenyl)-8-(4-methylpyridin-3-yl)imidazo[1,2-b]pyridazine (15); 3-(4-fluoro-2-(trifluoromethyl)phenyl)-8-(4-methylpyridin-3-yl)imidazo[1,2-b]pyridazine (16); 8-(4-methylpyridin-3-yl)-3-(2,4,5-trifluorophenyl)imidazo[1,2-b]pyridazine (17); 8-(4-methylpyridin-3-yl)-3-(pyrazin-2-yl)imidazo[1,2-b]pyridazine (18); 2-(8-(4-methylpyridin-3-yl)imidazo[1,2-b]pyridazin-3-yl)thiazole (19); 5-(8-(4-methylpyridin-3-yl)imidazo[1,2-b]pyridazin-3-yl)thiazole (20); 8-(4-methylpyridin-3-yl)-3-(pyridin-2-yl)imidazo[1,2-b]pyridazine (21); 8-(4-methylpyridin-3-yl)-3-vinylimidazo[1,2-b]pyridazine (22); 3-phenyl-8-(pyridin-3-yl)imidazo[1,2-b]pyridazine (23); 3-(4-fluoro-2-methylphenyl)-8-(pyridin-3-yl)imidazo[1,2-b]pyridazine (24); 3-(4-fluoro-2-methoxyphenyl)-8-(pyridin-3-yl)imidazo[1,2-b]pyridazine (25); 3-(4-fluorophenyl)-8-(pyridin-3-yl)imidazo[1,2-b]pyridazine (26); 3-(2-chloro-4-fluorophenyl)-8-(pyridin-3-yl)imidazo[1,2-b]pyridazine (27); 4-(3-(2-Chloro-4-fluorophenyl)imidazo[1,2-b]pyridazin-8-yl)isoquinoline (28); 4-(3-(2-(trifluoromethyl)pyridin-3-yl)imidazo[1,2-b]pyridazin-8-yl)isoquinoline (29); 4-(3-(4-fluorophenyl)imidazo[1,2-b]pyridazin-8-yl)isoquinoline (30); 3-(2,4-dichlorophenyl)-8-(4-methylpyridin-3-yl)imidazo[1,2-b]pyridazine (31); 8-(4-methylpyridin-3-yl)-3-(naphthalen-1-yl)imidazo[1,2-b]pyridazine (32); 3-(4-chlorophenyl)-8-(4-methylpyridin-3-yl)imidazo[1,2-b]pyridazine (33); 3-(3,5-dichlorophenyl)-8-(4-methylpyridin-3-yl)imidazo[1,2-b]pyridazine (34); 8-(4-methylpyridin-3-yl)-3-(thiophen-2-yl)imidazo[1,2-b]pyridazine (35); 8-(4-methylpyridin-3-yl)-3-(thiophen-3-yl)imidazo[1,2-b]pyridazine (36); 8-(4-methylpyridin-3-yl)-3-(3-(trifluoromethyl)phenyl)imidazo[1,2-b]pyridazine (37); 3-(3,5-dimethylphenyl)-8-(4-methylpyridin-3-yl)imidazo[1,2-b]pyridazine (38); 8-(4-methylpyridin-3-yl)-3-(2-(trifluoromethyl)phenyl)imidazo[1,2-b]pyridazine (39); 8-(4-methylpyridin-3-yl)-3-(pyridin-3-yl)imidazo[1,2-b]pyridazine (40); 3-(3,4-difluorophenyl)-8-(4-methylpyridin-3-yl)imidazo[1,2-b]pyridazine (41); 8-(4-methylpyridin-3-yl)-3-(2-phenoxyphenyl)imidazo[1,2-b]pyridazine (42); 3-(3,4-dimethylphenyl)-8-(4-methylpyridin-3-yl)imidazo[1,2-b]pyridazine (43); 8-(4-methylpyridin-3-yl)-3-(3-(methylthio)phenyl)imidazo[1,2-b]pyridazine (44); 8-(4-methylpyridin-3-yl)-3-(3-(trifluoromethoxy)phenyl)imidazo[1,2-b]pyridazine (45); 8-(4-methylpyridin-3-yl)-3-(2-(trifluoromethoxy)phenyl)imidazo[1,2-b]pyridazine (46); 8-(4-methylpyridin-3-yl)-3-(2-(phenoxymethyl)phenyl)imidazo[1,2-b]pyridazine (47); 3-(2,5-dichlorophenyl)-8-(4-methylpyridin-3-yl)imidazo[1,2-b]pyridazine (48); 3-(2,3-dimethylphenyl)-8-(4-methylpyridin-3-yl)imidazo[1,2-b]pyridazine (49); 3-(2,5-dimethylphenyl)-8-(4-methylpyridin-3-yl)imidazo[1,2-b]pyridazine (50); (2-(8-(4-methylpyridin-3-yl)imidazo[1,2-b]pyridazin-3-yl)phenyl)methanol (51); 3-(3-fluoro-5-methoxyphenyl)-8-(4-methylpyridin-3-yl)imidazo[1,2-b]pyridazine (52); 3-(8-(4-methylpyridin-3-yl)imidazo[1,2-b]pyridazin-3-yl)benzenesulfonamide (53); and 3-(4-fluorophenyl)-8-(4-methoxypyridin-3-yl)imidazo[1,2-b]pyridazine (54).

5. A pharmaceutical composition, comprising; a pharmaceutically acceptable carrier and a compound of claim 1 or pharmaceutically acceptable salts thereof.

6. The compound according to claim 3 wherein said compound is:

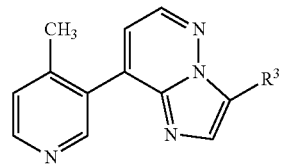

$R^3$ is phenyl substituted with zero to 3 $R^b$; and
each $R^b$ is independently —CH$_3$, —CF$_3$, —OCH$_3$, —OCF$_3$, F, and/or Cl.

7. The compound according to claim 6 wherein said compound is:

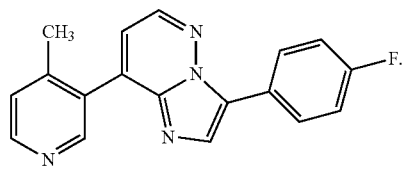 [SMILES: Cc1ccncc1-c1ccnn2c(-c3ccc(F)cc3)cnc12]

8. A method for treating cancer comprising administering a compound according to claim 1 or a pharmaceutically-acceptable salt thereof, to a patient in need thereof, wherein said cancer is prostate cancer; and wherein treating cancer is inhibiting, arresting, and/or relieving cancer.

* * * * *